(12) United States Patent
Cowan et al.

(10) Patent No.: US 10,060,758 B2
(45) Date of Patent: *Aug. 28, 2018

(54) ENCODING AND SENSING OF SYRINGE INFORMATION

(71) Applicant: Bayer Medical Care Inc., Indianola, PA (US)

(72) Inventors: Kevin P. Cowan, Allison Park, PA (US); John A. Brosovich, Pittsburgh, PA (US); Alan D. Hirschman, Glenshaw, PA (US); Barry Iddon, Jeannette, PA (US); Michael J. Yanniello, Cheswick, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 1021 days.

This patent is subject to a terminal disclaimer.

(21) Appl. No.: 14/329,050

(22) Filed: Jul. 11, 2014

(65) Prior Publication Data

US 2014/0358086 A1  Dec. 4, 2014

Related U.S. Application Data

(62) Division of application No. 11/254,061, filed on Oct. 19, 2005, now Pat. No. 8,821,450, which is a division
(Continued)

(51) Int. Cl.
*A61M 5/178* (2006.01)
*G01D 5/12* (2006.01)
(Continued)

(52) U.S. Cl.
CPC .............. *G01D 5/12* (2013.01); *A61M 5/1452* (2013.01); *A61M 5/3129* (2013.01);
(Continued)

(58) Field of Classification Search
CPC .............. A61M 5/3129; A61M 5/1452; A61M 5/14546; A61M 2005/3125; A61M 2205/6063

See application file for complete search history.

(56) References Cited

U.S. PATENT DOCUMENTS

| 4,006,736 A | 2/1977 | Kranys et al. |
| 4,278,086 A | 7/1981 | Hodgins et al. |

(Continued)

FOREIGN PATENT DOCUMENTS

| JP | 2000011721 A | 1/2000 |
| WO | 9425089 A1 | 11/1994 |

(Continued)

OTHER PUBLICATIONS

International Search Report for Counterpart PCT Application No. PCT/US2002/01052 dated Jan. 29, 2003.
(Continued)

*Primary Examiner* — Matthew F Desanto
(74) *Attorney, Agent, or Firm* — David Schramm; Joseph L. Kent; James R. Stevenson

(57) ABSTRACT

A syringe for use with a powered injector to inject a fluid into a patient that includes a length of material adapted to transmit or propagate electromagnetic energy therethrough. The length of material includes at least a first indicator positioned along the length of material. The first indicator is adapted to interact with at least a portion of the energy being propagated through the length of material in a manner that is detectable. The presence (or absence) of the first indicator provides or corresponds to information about the syringe configuration. The indicator(s) of the present invention can, for example, provide information about syringe configuration by the number and/or position thereof. A plurality or set of such syringes can be provided, with the configuration of
(Continued)

each such syringe being represented by the presence or absence of indicator(s) of that syringe.

11 Claims, 22 Drawing Sheets

Related U.S. Application Data of application No. 09/765,498, filed on Jan. 18, 2001, now Pat. No. 7,018,363.

(51) Int. Cl.
*A61M 5/145* (2006.01)
*A61M 5/31* (2006.01)

(52) U.S. Cl.
CPC ............... *A61M 2005/3125* (2013.01); *A61M 2205/6036* (2013.01); *A61M 2205/6063* (2013.01)

(56) References Cited

U.S. PATENT DOCUMENTS

| | | | |
|---|---|---|---|
| 4,650,475 A | 3/1987 | Smith et al. | |
| 4,978,335 A | 12/1990 | Arthur, III | |
| 5,066,859 A | 11/1991 | Karkar et al. | |
| 5,383,858 A | 1/1995 | Reilly et al. | |
| 5,461,239 A | 10/1995 | Atherton | |
| 5,520,653 A | 5/1996 | Reilly et al. | |
| 5,531,698 A * | 7/1996 | Olsen .................... | A61M 5/142 128/DIG. 12 |
| 5,545,140 A | 8/1996 | Conero et al. | |
| 5,662,612 A | 9/1997 | Niehoff | |
| 5,741,232 A | 4/1998 | Reilly et al. | |
| 5,806,519 A | 9/1998 | Evans, III et al. | |
| 5,843,037 A | 12/1998 | Uber, III | |
| 5,873,861 A | 2/1999 | Hitchins et al. | |
| 5,916,197 A | 6/1999 | Reilly et al. | |
| 5,928,197 A | 7/1999 | Niehoff | |
| 5,944,694 A | 8/1999 | Hitchins et al. | |
| 5,954,700 A | 9/1999 | Kovelman | |
| 5,997,502 A | 12/1999 | Reilly et al. | |
| 6,004,292 A * | 12/1999 | Battiato ............ | A61M 5/14546 128/DIG. 1 |
| 6,019,745 A | 2/2000 | Gray | |
| 6,090,064 A | 7/2000 | Reilly et al. | |
| 6,090,864 A | 7/2000 | Narayan et al. | |
| 6,221,051 B1 | 4/2001 | Hjertman et al. | |
| 6,336,913 B1 | 1/2002 | Spohn et al. | |
| 6,533,183 B2 | 3/2003 | Aasmul et al. | |
| 6,726,657 B1 | 4/2004 | Dedig et al. | |
| 6,733,478 B2 | 5/2004 | Reilly et al. | |
| 6,743,202 B2 | 6/2004 | Hirschman et al. | |
| 6,958,053 B1 | 10/2005 | Reilly | |
| 7,018,363 B2 * | 3/2006 | Cowan ................ | A61M 5/1452 604/151 |
| 7,462,166 B2 | 12/2008 | Cowan et al. | |
| 8,439,876 B2 | 5/2013 | Spohn et al. | |
| 8,821,450 B2 * | 9/2014 | Cowan ................ | A61M 5/1452 604/151 |
| 2001/0034506 A1 | 10/2001 | Hirschman et al. | |
| 2002/0000471 A1 | 1/2002 | Aasmul et al. | |
| 2002/0128606 A1 | 9/2002 | Cowan et al. | |
| 2003/0060754 A1 | 3/2003 | Reilly et al. | |
| 2003/0065287 A1 | 4/2003 | Spohn et al. | |
| 2004/0064101 A1 | 4/2004 | Kowan et al. | |
| 2006/0129104 A1 | 6/2006 | Cowan et al. | |

FOREIGN PATENT DOCUMENTS

| | | |
|---|---|---|
| WO | 9702059 A1 | 1/1997 |
| WO | 9800187 A1 | 1/1998 |
| WO | 9965548 A1 | 12/1999 |
| WO | 0137903 A2 | 5/2001 |

OTHER PUBLICATIONS

International Search Report for PCT Application No. PCT/US2002/010398 dated Aug. 1, 2002.

*LF* vs. *Medrad, Inc.* Civil Action No. C-1-98-858 pp. A6241 R-A6251 R; Redacted Post-Claim Construction Declaration of Thomas H. Braunstein (Nov. 19, 2001).

"Second Post-Claim Construction Declaration of Thomas H.Braunstein (Dec. 7, 2001)."

\* cited by examiner

1120

ENCODING AND SENSING OF SYRINGE INFORMATION

CROSS REFERENCE TO RELATED APPLICATION

This application is a division of application Ser. No. 11/254,061, filed on Oct. 19, 2005, now U.S. Pat. No. 8,821,450, which is a division of application Ser. No. 09/765,498, filed on Jan. 18, 2001, now U.S. Pat. No. 7,018,363, the contents of which are hereby incorporated by reference.

FIELD OF THE INVENTION

The present invention relates to encoding and sensing of information or configuration, and, especially, to syringes and syringe encoders having encoding of information relevant to medical injection procedure, to injector systems including syringe encoding and to methods of encoding and sensing syringe information.

BACKGROUND OF THE INVENTION

Critical parameters of an injection procedure are determined by a number of variables, including, for example, syringe diameter, syringe length, syringe material and fluid composition/concentration. Among the affected injection procedure parameters are fluid volume delivered, flow rate, fluid pressure, and limits of injector piston travel. In current injector systems, syringe size is generally determined either (1) manually by action of an operator who enters the syringe size or type into the injector software, or (2) automatically by means of switches on the injector head which are mechanically coupled to raised or sunken elements on the syringe. See, for example, U.S. Pat. Nos. 5,741,232, 6,090,064 and 5,873,861, assigned to the assignee of the present application, the disclosures of which are incorporated herein by reference. FIG. 1A illustrate sunken elements or detents 2 and 2' positioned around the arc of flanges 3 and 3' in a rear, engagement flange portion of a syringe 4 as described in U.S. Pat. No. 5,873,861. Syringes 4, including detents 2 and 2', have been fabricated from, for example, clear or opaque, polymeric materials. Detents 2 and/or 2' cooperate with one or more correspondingly positioned switches 6 in a powered injector 8 illustrated in FIG. 1B. The presence or absence of one or more detents provides a code that represents syringe configuration.

Constraints of mechanical and electrical design, however, limit the number of such automatic detection switches. Indeed, only limited syringe configurations are automatically detected with present systems. Additionally, failure of moving mechanisms is also a problem. Moreover, certain electrical and mechanical encoding systems can significantly increase manufacturing costs of a syringe and/or injector. Other currently available methods of encoding and sensing syringe configuration include the placement of bar codes and corresponding sensors upon the syringe and injector, respectively, as disclosed in U.S. Pat. No. 5,997,502. Bar code systems, however, suffer from some of the same problems as the electromechanical systems discussed above.

As used herein, the term "syringe configuration" is used to encompass all information about a particular syringe, including, but not limited to, information about the mechanical properties of a syringe (for example, material, length and diameter) as well as information about the contents of the syringe (for example, volume and composition). With the advent of new syringes, and especially prefilled syringes, the need to accurately encode and sense (or read) syringe configuration variables is heightened. The information on syringe configuration can be used by a powered injector to control the injection procedure as a function of defined syringe configuration/injection parameters. Moreover, a record of data associated with an injection procedure may be kept, for example, to satisfy accurate billing and cost information requirements under managed health care. A record may be maintained of information such as the type of syringe used, the amount of contrast medium used, the type of contrast medium used, the sterilization date, the expiration date, lot codes, the properties of the contrast media, and/or other clinically relevant information. Such information can be recorded digitally for sharing with computerized hospital billing systems, inventory systems, control systems etc.

It is very desirable for a syringe-based injector system to automatically determine such information. It is, therefore, an object of this invention to provide encoding of information to be shared between a syringe and a powered injector for use therewith.

SUMMARY OF THE INVENTION

In one aspect, the present invention provides a syringe for use with a powered injector to inject a fluid into a patient that includes a length of material adapted to transmit or propagate electromagnetic energy therethrough or through the length thereof. The length of material includes at least a first indicator positioned along the length of material. The first indicator is adapted to interact with at least a portion of the energy propagated through the length of material in a manner that is detectable. The presence (or absence) of the first indicator provides or corresponds to information about the syringe configuration. The indicator(s) of the present invention can, for example, provide information about syringe configuration by the number and/or position thereof. A plurality or set of such syringes can be provided, with the configuration of each such syringe being represented by the presence, absence and/or positioning of indicator(s) of that syringe.

As used herein with respect to the information provided by the indicators, the terms "position," "positioning" and related terms refer to absolute and/or relative position. In that regard, information can be provided by the absolute position of one or more indicators upon the length of material. As used herein, the term absolute position refers to the position of the indicator(s) on the length material with respect to a reference position (for example, a fixed position on the length of material or on a powered injector). Information can also be provided by the relative positions of a plurality of indicators with respect to each other independent of their absolute positions upon the length of material.

As used herein in connection with electromagnetic energy transmitted or propagated through the length of material, the phrase "interact with" refers generally to, for example, a transmission of the energy, a change in the direction of the energy, a change in the intensity of the energy, a change in the speed of travel of the energy and/or a change in form of the energy being propagated through the length of material. Such interactions are preferably readily detectable, for example, using sensors as known in the art. For example, the indicator can be adapted to transmit the energy impinging thereupon without modification thereof, or can be adapted to transform, refract, scatter and/or absorb at least a portion of the energy. In general, the indicators of the present invention are discontinuities or areas having properties different from the remainder of the length of material such that the energy impinging upon an indicator interacts differently from energy that impinges upon a portion of the length of material not including an indicator. This different interaction of the indicator with impinging energy is detectable. For example, an indicator can be an area of the length of material through which energy can be transmitted outside of the length of material whereas the remainder of the length of material prevents transmission of energy outside of length of material. In the case of light energy, for example, indicators can be discontinuities such as angled surfaces formed in the length of material that, for example, refract, reflect, scatter or absorb light energy. Indicators can also include a detection material (for example, a fluorescent material) that is placed in a detectable state upon impingement of the energy.

Preferably, the syringe includes a plurality of indicators (that is, preferably at least two indicators) along the length of the material positioned at unique predetermined positions (that is, absolute and/or relative positions). Each of the indicators is adapted to interact with or to modify at least a portion of the energy being transmitted or propagated through the length of material in a manner that is detectable as described above. The number of indicators can provide information of syringe configuration. Likewise, predetermined positions of the indicators can provide information about syringe configuration. For example, a binary/digital code can be set forth by the presence/absence of indicators at predetermined positions. Multiple, binary codes can be placed on a single syringe using groups or sets of indicators at different positions upon the syringe.

In one embodiment, the electromagnetic energy is light energy and the length of material can, for example, have a refractive index greater than the refractive index of an adjacent environment such that light energy can be internally reflected in the material along its length. Internal reflectance assists in efficiently propagating light energy through the length of the material. Indicators suitable for use with light energy include, for example, angled surfaces in the syringe wall adapted to refract and/or reflect light energy outside of the syringe wall.

The length of material can, for example, be formed integrally with the syringe. In one such embodiment, the length of material is a translucent portion of the syringe wall. Likewise, the length of material can also be separate from the syringe. The length of material can, for example, be associated with or attachable to the syringe. The length of material can also form part of a syringe adapter designed to adapt a syringe for use with a particular injector or part of a heater jacket used to warm contrast within a syringe as known in the art.

In another aspect, the present invention provides a syringe encoder for use with a powered injector to inject a fluid into a patient. The syringe encoder includes a length of material adapted to transmit or propagate electromagnetic energy therethrough. The length of material includes at least a first indicator positioned along the length of material. As discussed above, the first indicator is adapted to interact with at least a portion of the energy being transmitted or propagated through the length of material in a manner that is detectable to provide information about the syringe configuration. The syringe encoder can, for example, be formed integrally with, be associated with (for example, shipped in the same container), or be attachable to a syringe or a syringe adapter (designed to adapt a particular syringe for use with a powered injector).

In another aspect, the present invention provides an injector system for use with a syringe including: a powered injector having a powered drive member. The injector system also includes at least one source of electromagnetic energy and at least one sensor. The injectors system further includes a syringe encoder as described above. In that regard, the syringe encoder includes a length of material adapted to transmit or propagate electromagnetic energy therethrough. The length of material includes at least a first indicator along the length of material that is adapted to interact with at least a portion of the energy transmitted or propagated through the length of material in a manner that is detectable by the sensor.

In another aspect, the present invention provides an encoder system including at least one source or electromagnetic energy and at least one sensor. The encoder system further includes a syringe encoder as described above. In that regard, the syringe encoder includes a length of material adapted to propagate electromagnetic energy therethrough. The length of material includes at least a first indicator along the length of material that is adapted to interact with at least a portion of the energy being transmitted or propagated through the length of material in a manner that is detectable by the sensor.

In a further aspect, the present invention provides a method of encoding information about syringe configuration. The method includes the steps of: transmitting or propagating energy through a least a portion of a length of material, providing at least a first indicator adapted to interact with at least a portion of the energy being transmitted or propagated through the length of material in a manner that is detectable along the length of material, and detecting the interaction of at least a portion of the energy with the first indicator. As described above, a predetermined position of one or more indicators can be used to provide information about syringe configuration.

The encoders and methods of the present invention are not limited to use with syringes or in medical injection procedures. Such encoders can be used with other pumps, pressurizing mechanisms or other fluid path elements used in medical injection procedures such as the pumps and fluid path elements disclosed, for example, in U.S. Pat. Nos. 5,806,519, 5,843,037 and 5,916,197, assigned to the assignee of the present invention, the disclosures of which are incorporated herein by reference. Indeed, the encoders and methods of the present invention are well suited for any use in which it is desirable to encode information in the medical arts or in other fields of use. In another aspect, the present invention thus provides an encoder including a length of material adapted to transmit or propagate electromagnetic energy therethrough. The length of material includes at least a first indicator positioned along the length of material. As discussed above, the first indicator is adapted to interact with at least a portion of the energy being transmitted or propagated through the length of material in a manner that is detectable to provide information.

Likewise, the present invention provides a method of encoding information including the steps of: transmitting or propagating energy through a least a portion of a length of material, providing at least a first indicator adapted to interact with at least a portion of the energy being transmitted or propagated through the length of material in a manner that is detectable along the length of material, and detecting the interaction of at least a portion of the energy with the first indicator. As described above, a predetermined position (relative position and/or absolute position) of one or more indicators can be used to provide information.

The encoding schemes of the present invention provide a reliable manner of encoding information of, for example, syringe configuration. Mechanically movable mechanisms are not required, resulting in increased reliability as compared to many prior encoding schemes. Moreover, the syringe encoders of the present invention are readily formed integrally with, for example, a syringe or a syringe adapter, resulting in less costly manufacture than many prior encoding mechanisms.

Furthermore, the encoding systems, devices and methods of the present invention are well suited for use in magnetic resonance environment in which care must be taken to prevent failure of the encoding system or device and to prevent interference with the magnetic resonance imaging equipment. In that regard, the strong magnetic field in a magnetic resonance environment can adversely affect certain types of devices such as electromechanically activated devices. Furthermore, differences in magnetic permeability of materials within such devices and induced eddy currents therein can affect the homogeneity of the MRI magnetic field, generating image artifacts. Likewise, radio frequency energy generated by certain devices can induce unwanted artifacts upon the acquired MRI images. Such problems are easily avoided in the syringe encoding systems, devices and methods of the present invention. For example, electromechanical and other actuators are unnecessary in the present invention as no moving elements are required. Moreover, electromechanical energy used in the encoding systems, devices and methods of the present invention is easily selected to prevent interference with magnetic resonance equipment as well as interference from the magnetic resonance equipment. For example, light energy in the infrared, visible or ultraviolet range of the spectrum can be used. Likewise, radio frequency energy outside of frequency range of the MRI scanner can be used.

DETAILED DESCRIPTION OF THE INVENTION

The encoders, encoding systems and encoding methods of the present invention are particular useful in encoding information of configuration for syringes and other pumping mechanisms used in medical injection procedures. Several representative embodiments of the present invention in which light energy is used in connection with syringe encoders are discussed below.

In the case that light energy is used in the present invention, one can, for example, take advantage of the properties of light refraction/reflection at an interface between two different media to assist in efficiently propagating light through the length of the media having the higher refractive index. These different media can, for example, be a translucent or transparent syringe wall and the air surrounding the syringe wall.

Figure 1A:
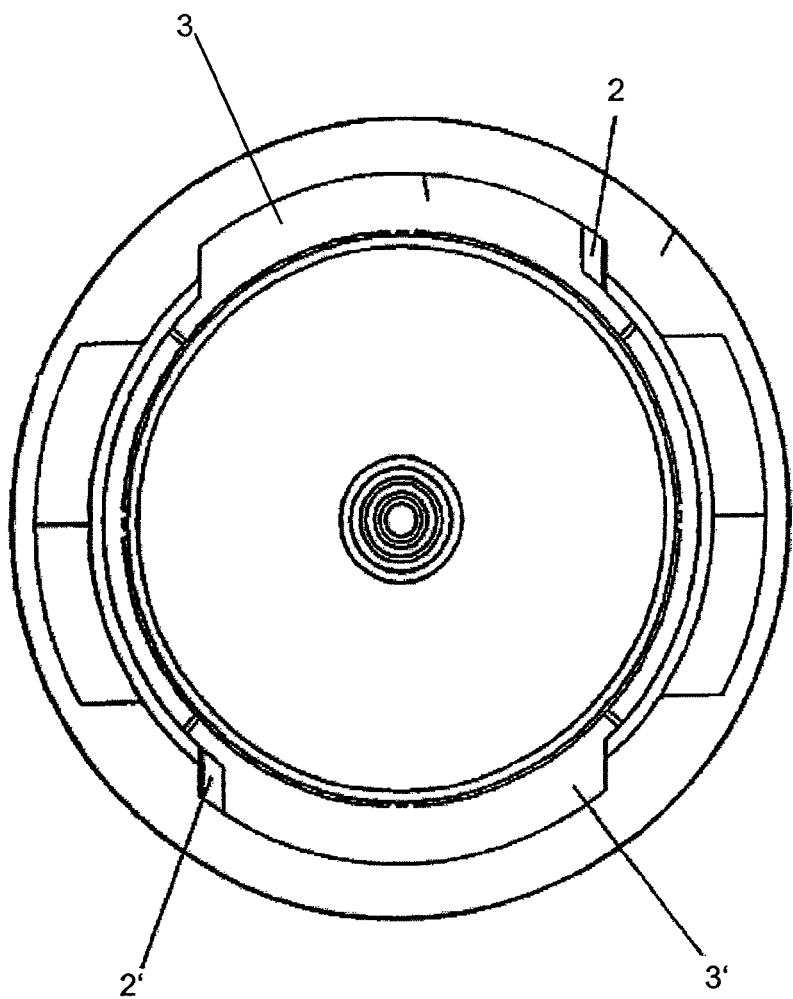
FIG. 1A illustrates a rear plan view of a currently available syringe including detents for providing syringe configuration information.
Figure 1B:
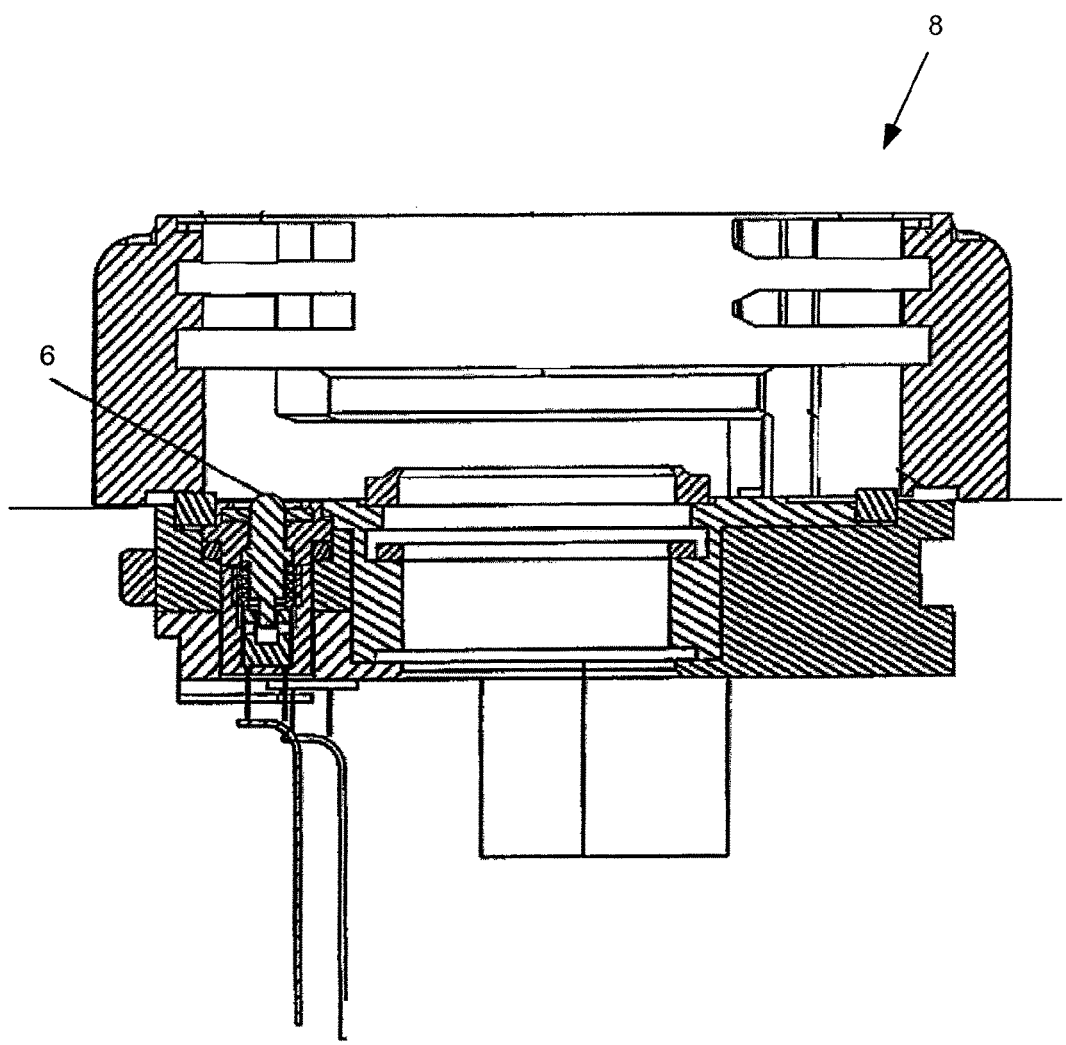
FIG. 1B illustrates a side cross-sectional view of the front portion of a currently available injector including electromechanical switches to cooperates with the detents of FIG. 1A.
Figure 2A:
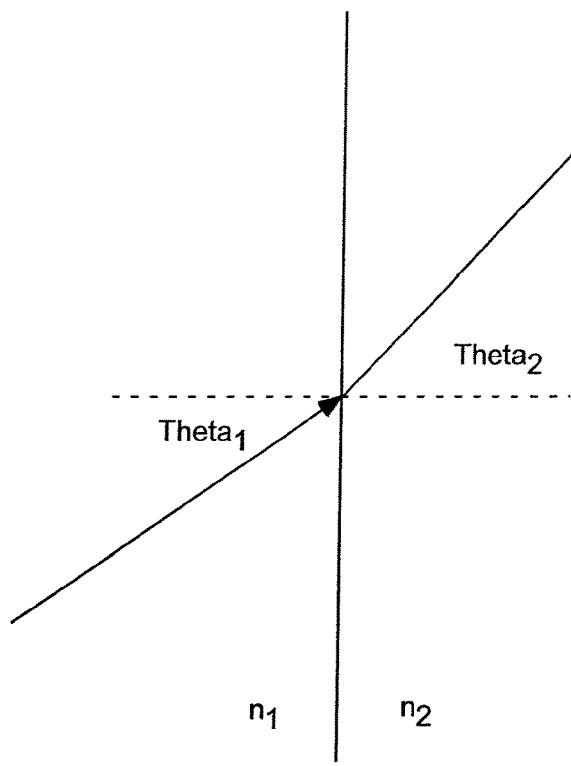
FIG. 2A illustrates the behavior of light energy incident upon an interface between two media having different refractive indices as provided by Snell's law.

The refraction of light at an interface between two dielectric media is governed by Snell's Law as follows:

$$n_1 \sin \theta_1 = n_2 \sin \theta_2$$

wherein $n_1$ and $n_2$ are the refractive indices of each dielectric material and θ or Theta is the angle of incidence of the light (as measured with respect to an orientation or plane normal to the interface). Snell's law is represented graphically in FIG. 2A.

Figure 2B:
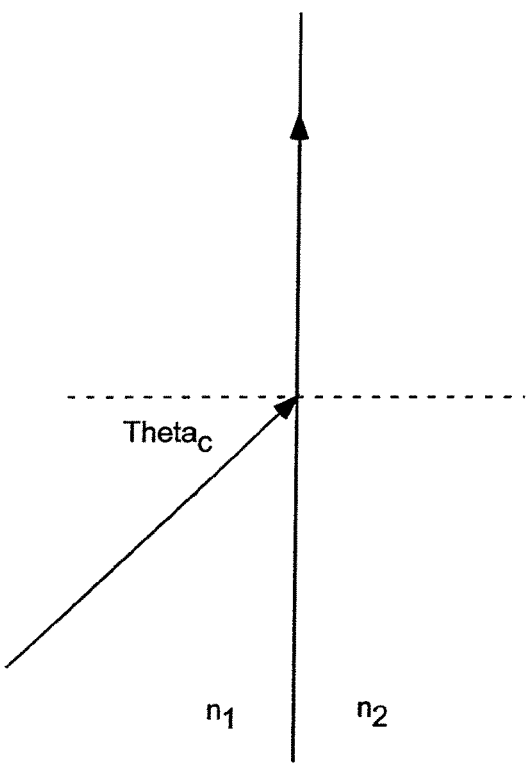
FIG. 2B illustrates the behavior of light incident upon an interface at a critical angle to result in theoretically total internal reflectance.

In the special case where light is initially traveling in a material with a higher index of refraction, and then encounters a region of lower index of refraction, the potential for the light to be reflected (internally within the first material) at the interface boundary arises. A critical angle can be defined in the following manner: any light that encounters the dielectric interface at an angle less than the critical angle will not be reflected at the interface—it will proceed on into the second medium. In other words, the angle of refraction at the critical angle is 90°. Mathematically, the critical angle is given by $$n_1 \sin \theta_1 = n_2$$
$$\theta_c = \sin^{-1}\left(\frac{n_2}{n_1}\right)$$

where $n_1$ and $n_2$ are the refractive indices of each dielectric material and $\theta_c$ or $Theta_c$ is the critical angle of incidence of the light. The critical angle of incidence is illustrated graphically in FIG. 2B.

Figure 2C:
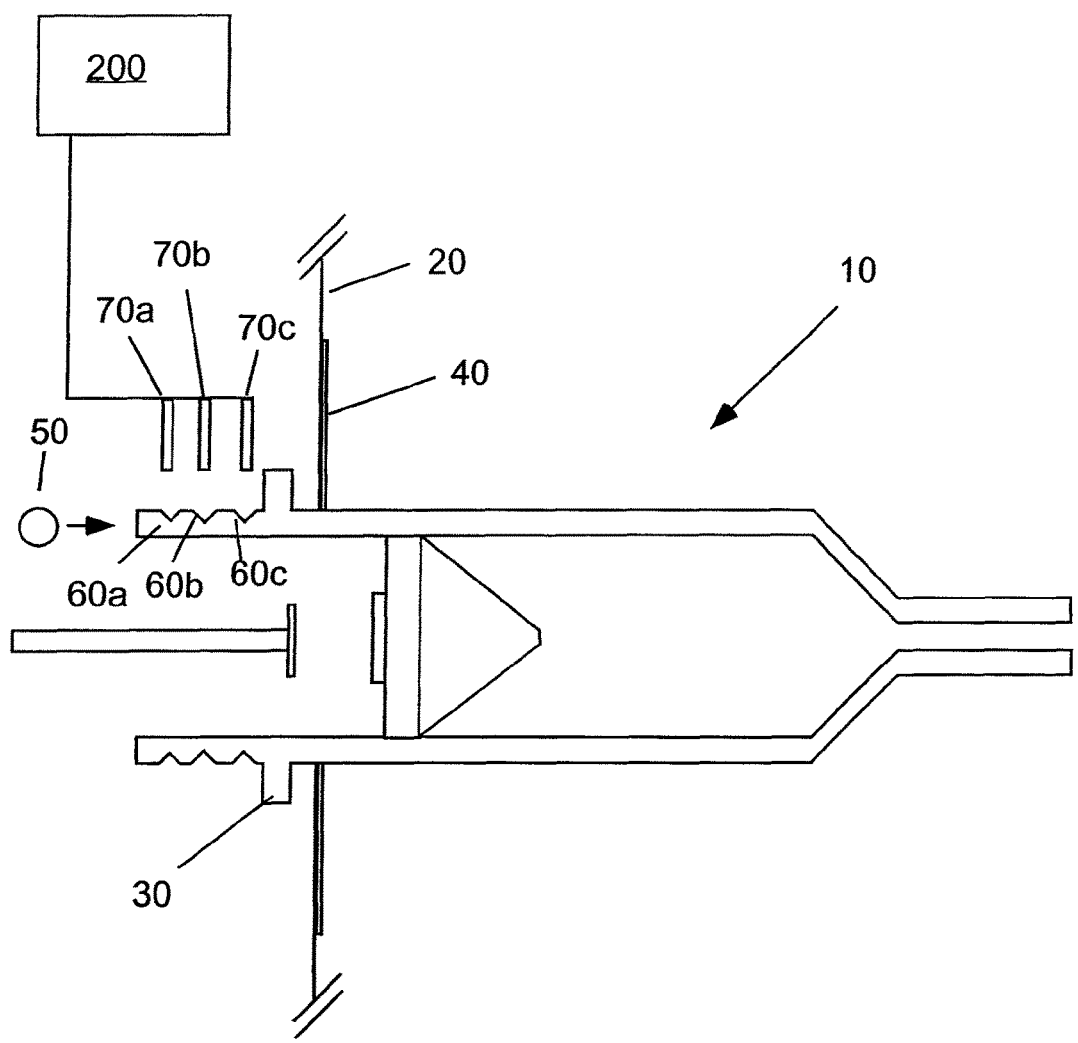
FIG. 2C illustrates a side cross-sectional view of an embodiment of a syringe encoding system of the present invention.

FIG. 2C illustrates a syringe 10 having at least a portion thereof formed from a generally translucent or transparent material such as glass or a clear plastic. Syringe 10 can, for example, be removably positioned upon a powered injector 20 by the interaction of syringe flange(s) 30 and drip flange 40 as with mounting means on and/or in the front wall of injector 20 as described, for example, in U.S. Pat. No. 5,997,502. A light source 50 is, for example, positioned within injector 20 to transmit or propagate light energy in a generally axial direction (that is, parallel to the axis of syringe 10) through the wall of syringe 10. The light energy can be outside the wavelength of visible light to reduce interference from ambient light. Light source 50 can also be pulsed to improve detectability.

Figure 2D:
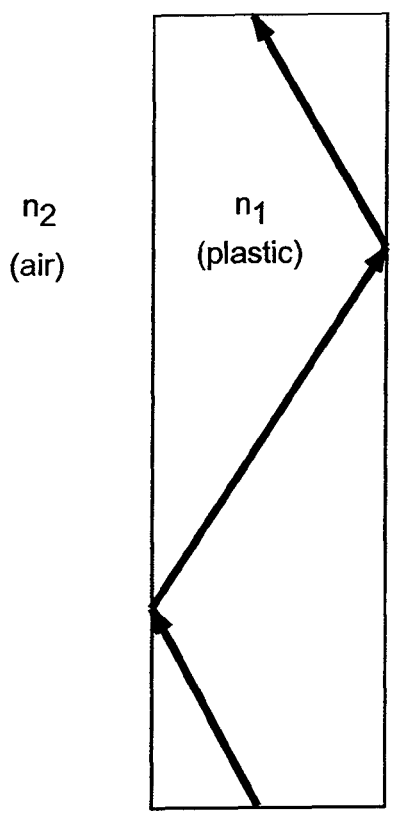
FIG. 2D illustrates total internal reflectance of light within the syringe wall material.

FIG. 2D illustrates light being internally reflected within the syringe wall. In general, all light striking the interface between the syringe wall and the air at an angle greater that the critical angle (as measured from a vertical plane in the orientation of FIG. 2C or as measured from a horizontal plane in the orientation of FIG. 2D—that is, a plane normal to the syringe-air interface) will be internally reflected within the syringe wall and propagate therethrough in generally axial direction.

In one embodiment, syringe 10 was manufactured from polyethylene terephthalate (PET), for which the index of refraction measured at 632.8 nm (Helium-Neon laser output) is approximately 1.68 for an ambient temperature of 21° C. Given a refractive index of approximately 1.00 for air, this material resulted in a critical angle for the air-syringe interface of approximately 37° degrees. Therefore, if the light hits the interface at an angle greater than this value, it will be internally reflected. In the case of no scattering or absorption, this reflection is theoretically perfect. Indeed, measurements have shown that the reflection coefficient from a dielectric interface within, for example, a high quality optical fiber exceeds 0.9999. See, for example, *Handbook of Optics*, McGraw-Hill, p. 13-6. In practice, the reflection coefficient will decrease as imperfections in the material increase.

Given the approximately 37° critical angle for the syringe-air interface, light being internally reflected within the plastic of the syringe wall is striking the interface at angles greater than or equal to the critical angle. Light that strikes the interface at a numerically "shallower" or smaller value will be transmitted through the interface out into the air.

Figure 2E:
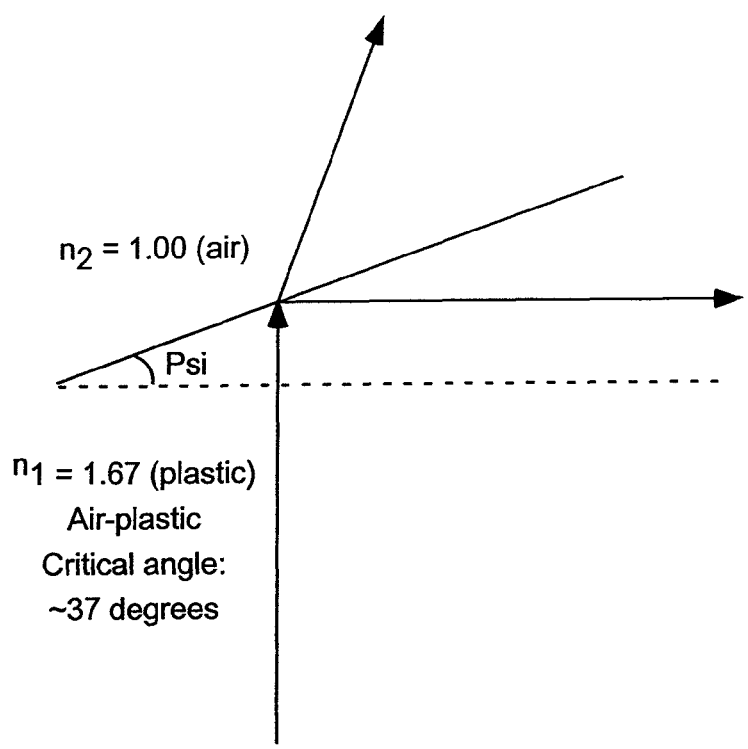
FIG. 2E illustrates the use of angled surfaces within the syringe to transmit light outside the syringe wall at a predetermined location.

FIG. 2E illustrates the case of light vertically propagating within the syringe wall encountering a beveled or angle interface. Not all of the light is reflected at the angled interface. In the case of LED emissions, for example, the light output is typically Gaussian with additional "misdirection" of the photons occurring as the light is scattered within the plastic. The net result is a packet, or cone, of light that is propagating within the plastic. When this cone of light strikes the angled interface, some of the light will continue through the interface into the air. In FIG. 2E, if the angle Psi exceeds the critical angle (37°), light will be reflected from the interface. If that light then encounters another angled interface, some of the light will be directed back into the plastic where it will again propagate until it hits the next angled interface. This scenario provides a slight increase in the total amount of light being redirected within the syringe wall (that is, to the right in the orientation of FIG. 2E) while also spatially distributing the light. The number of angled interfaces (for example, grooves, notches or raised features) that provides optimum light redirection can be readily calculated given the material properties, the angle(s) of the angled interfaces and nature of the light source.

In FIG. 2C, syringe 10 includes a series of indicators that are formed as angled surfaces or notches 60a-60c. The angled surfaces or indicator notches 60a-60c act as portals to transmit a portion of the light being propagated through the syringe wall into the surrounding air. Light sensors 70a-70c are positioned adjacent notches 60a-60c, respectively. The presence or absence of one or more of notches 60a-60c (or the relative positions of notches 60a-60c with respect to each other) can, for example, represent a binary or other code that corresponds to a particular syringe configuration (for example, a certain volume syringe containing a certain concentration of a particular type of contrast medium) as, for example, interpreted by a processing unit 200 in communicative connection with sensors 70a-70c. Notches 60a-60c can be placed relatively close to light source 50 to ensure that the amount of light transmitted into the surrounding air is measurable. In that regard, the total light energy available for measurement will decrease as the distance from light source 50 increases (for example, via scattering, absorption and/or transmission through angled surfaces 60a-60c). Notches 60a-60c can be formed around the circumference of syringe 10. In this manner, the orientation of syringe 10 (that is, the degree of rotation about its axis) is irrelevant to the ability of sensors 70a-70c to measure light transmitted from syringe 10.

Positioning indicators (for example, indicators 60a-60c of FIG. 2C) in general alignment parallel to the axial orientation of syringe 10 and propagating energy from source 50 through the syringe wall generally parallel to the axis of syringe 10, provides substantial space for multiple indicators along the length of syringe 10 and reduces or eliminates problems in propagating energy that can arise from the curvature of the syringe wall around the axis of syringe 10. Moreover, this orientation facilitates positioning of energy source 50 and sensors 70a-70c with only minor changes in existing syringe and injector designs.

Figure 2F:
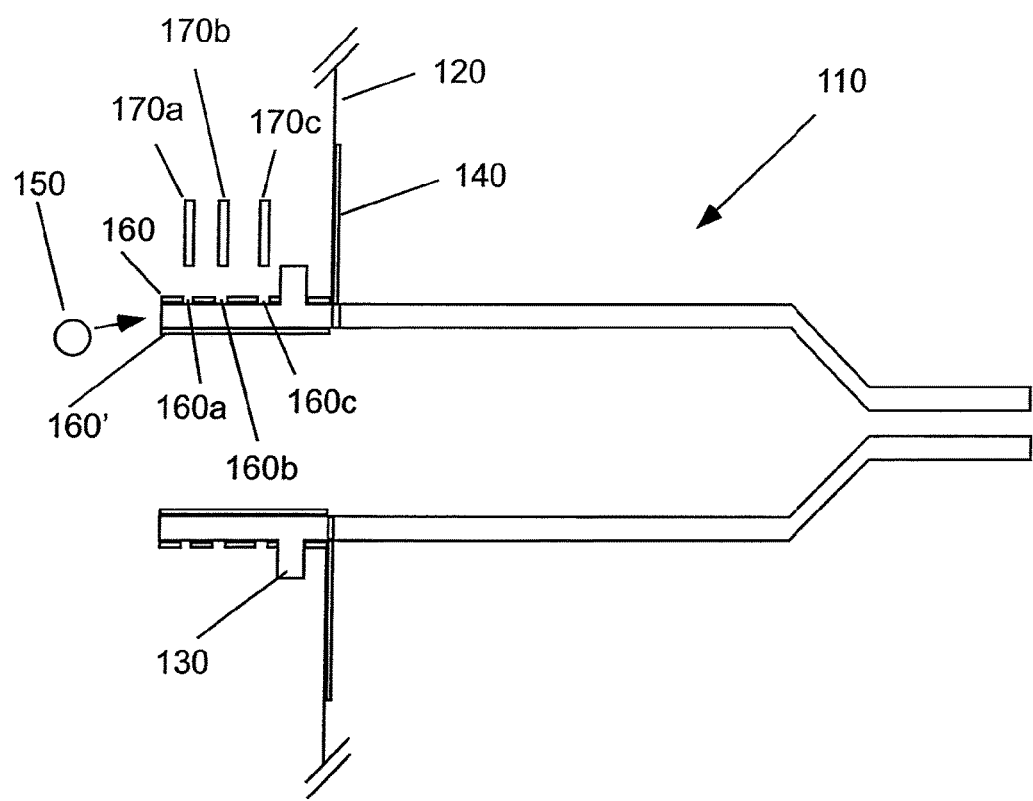
FIG. 2F illustrates a side cross-sectional view of another embodiment of a syringe encoding system of the present invention.

FIG. 2F illustrates an alternative embodiment of a syringe 110 attached to a powered injector 120. As discussed above, syringe 110 includes a mounting flange 130 and a drip flange 140. Injector 120 includes a light source 150 positioned to transmit light into the syringe wall so that light propagates through the syringe wall in a generally axial direction. In this embodiment, at least the rearward section of syringe 110 includes a shield or barrier 160 that is placed at least on the exterior perimeter of syringe 110. Shield 160 includes several indicators formed as openings or portals 160a-c that allow light to be transmitted into the surrounding air whereas the remainder of shield 160 prevents light from being transmitted therethrough. Such light transmitted into the surrounding air can be detected by sensors 170a-170c as discussed above to provide information regarding the syringe configuration. A shield 160' can also be provided on the interior diameter of the syringe wall. Shields 160 and 160' can, for example, be an opaque plastic or an opaque ink. Shields 160 and 160' can also be reflective to ensure that light is propagated axially in an efficient manner.

Although internal reflectance arising from materials of different refractive indices as described above is useful in efficiently propagating light energy through the length of a medium, internal reflectance is not necessary in practicing the present invention. For example, reflective shields or linings as described in connection with FIG. 2F can be used to propagate light energy through a length of material. Moreover, those light rays propagating through a length of material generally parallel to the axis of the length of material (without internal reflection) can interact with indicators of the present invention in a detectable manner.

In several embodiments of the present invention, steps are preferably taken to prevent interference from background or ambient light (that is, light not originating from the light source(s)). For example, narrow bandwidth detection can be used in which the light source(s) and sensor(s) operate over a very narrow range of optical wavelengths. Moreover, synchronous detection can be used in which the light source(s) are modulated at some frequency and the sensor electronics are selectively sensitive to signals varying at that frequency. At the simplest level, the difference in detected signal between a source on state and a source off state is measured. Many other detection schemes as known, for example, in the optical detection arts are suitable for use in the present invention.

In the embodiments of FIGS. 2C and 2F, all indicators for directing/transmitting light to sensors are located in or on the syringe wall, to the rear of drip flanges 40 and 140. As clear to those skilled in the art, such indicator/sensor pairing can be located anywhere along the syringe wall. Moreover, the syringe can include a portion or member that is separate from the syringe wall through which energy can be transmitted for syringe information encoding.

FIGS. 3A through 3E illustrate several further embodiments of the present invention. Each of FIGS. 3A through 3E illustrates a length of material through which electromagnetic energy (for example, light energy) can pass or propagate. The length of material can for example be a portion of a syringe wall, a portion of a syringe adapter or a portion of a syringe or other encoder that is, for example, associated with and/or attachable to syringe, a syringe adapter (for example, a sleeve that is positioned adjacent to or that fits over a syringe or a syringe adapter) or another device to be encoded. Examples of adapters suitable for use in the present invention are disclosed, for example, in U.S. patent application Ser. No. 09/365,285 filed Jul. 30, 1999 and in U.S. patent application Ser. No. 09/633,299 filed Aug. 8, 2000, assigned to the assignee of the present invention, the disclosures of which are incorporated herein by reference. In general, adapters enable use of syringes not specifically designed for use with a particular injector.

Figure 3A:
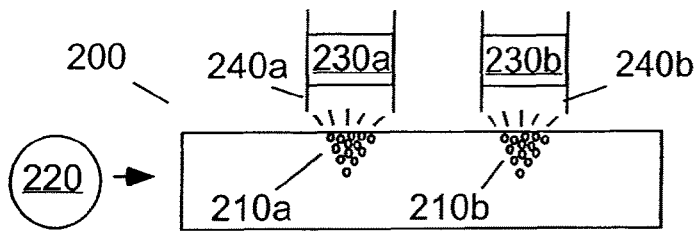
FIG. 3A illustrates a side cross-sectional view of an embodiment of a syringe encoder in which an indicator scatters light to be detected by corresponding sensor.

The lengths of material of FIGS. 3A through 3E are referred to simply as a syringe encoders below. In FIG. 3A, syringe encoder 200 includes indicators 210a and 210b that are discontinuities in syringe encoder 200 that act to transmit/redirect/scatter light propagating through syringe encoder 200 from light source 220. Such discontinuities can, for example, be formed as irregularities within the material of syringe encoder 200 or by incorporating another material within syringe encoder 200 (such as by coextrusion of polymeric materials). Light transmitted/redirected/scattered from indicators 210a and 210b is detected by sensors 230a and 230b, respectively. In the embodiment of FIG. 3A, sensors 230a and 230b are surrounded by shields or columnators 240a and 240b, respectively. Shields 240a and 240b extend toward the surface of syringe encoder 200 to reduce or prevent light transmitted/redirected/scattered from indicator 220b from being detected by sensor 230a and to prevent light transmitted/redirected/scattered from indicator 220a from being detected by sensor 230b, respectively (sometimes referred to as "crosstalk").

Figure 3B:
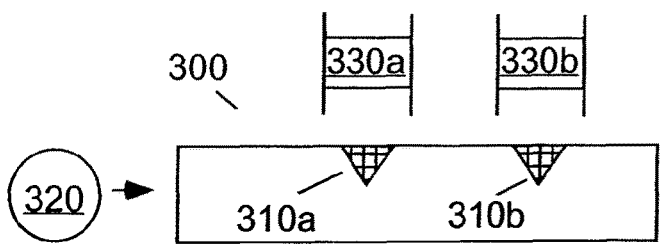
FIG. 3B illustrates a side cross-sectional view of an embodiment of a syringe encoder in which an indicator absorbs light.

In FIG. 3B, syringe encoder 300 includes indicators 310a and 310b that absorb light energy propagated through syringe encoder 300 from light source 320 that would otherwise be transmitted outside of syringe encoder 300. Sensors 330a and 330b detect the presence or absence of indicators 310a and 310b as described above. In this embodiment, however, the presence of an indicator at a predetermined position results in the absence of a signal at that position. Whereas indicators 210a and 210b of syringe encoder 200 may, for example, correspond to a binary code of 11, indicators 310a and 310b of syringe encoder 300 may correspond to a binary code of 00.

Figure 3C:
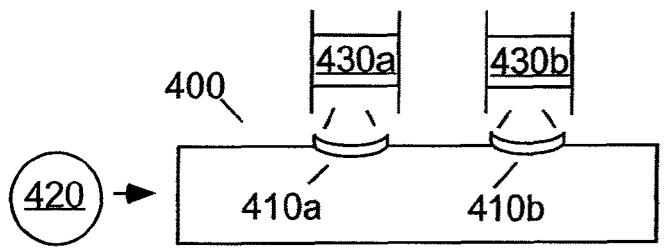
FIG. 3C illustrates a side cross-sectional view of an embodiment of a syringe encoder in which an indicator acts as a lens to focus light upon a corresponding sensor.

Syringe encoder 400 of FIG. 3C includes indicators 410a and 410b that act as lenses to focus light being propagated through syringe encoder 400 from light source 420 on sensors 430a and 430b, respectively.

Figure 3D:
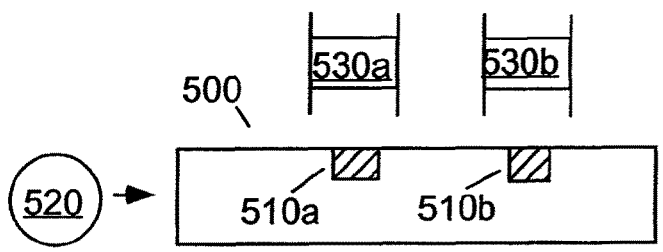
FIG. 3D illustrates a side cross-sectional view of an embodiment of a syringe encoder in which an indicator enters into an "excited" state detectable by a corresponding sensor when the indicator is contacted by electromagnetic energy.
Figure 3E:
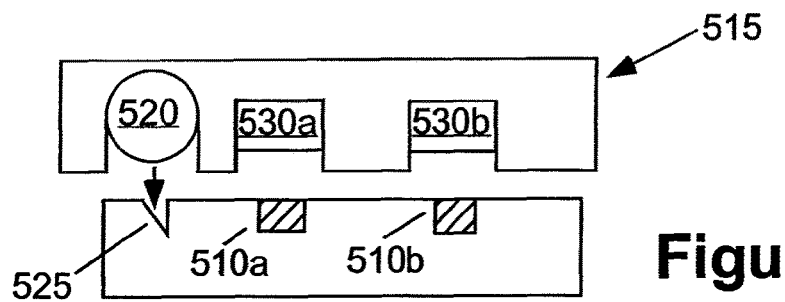
FIG. 3E illustrates a side cross-sectional view of another embodiment of the syringe encoder of FIG. 3D in which a source of light energy is placed in generally the same plane as the sensors thereof.

Syringe encoder 500 of FIG. 3D includes indicators 510a and 510b that are placed in an excited state when light from light source 520 impinges thereupon. For example, indicators 510a and 510b can include a material that fluoresces when light energy impinges thereupon. The excited state (for example, fluorescence) of indicators 510a and 510b is detectable by sensors 530a and 530b, respectively. Syringe encoder 500' of FIG. 3E is similar in operation to that of syringe encoder 500. However, in the embodiment of syringe encoder 500', light source 520 is placed in generally the same plane as sensors 530a and 530b. Light from light source 520 is redirected to propagate through syringe encoder 500' by angled surface 525. Moreover, in the embodiment of FIG. 3E, light source 520 and sensors 530*a* and 530*b* are incorporated in a carrier 515, which can, for example, be cylindrical sheath such as a syringe heater as known in the art.

Figure 4:
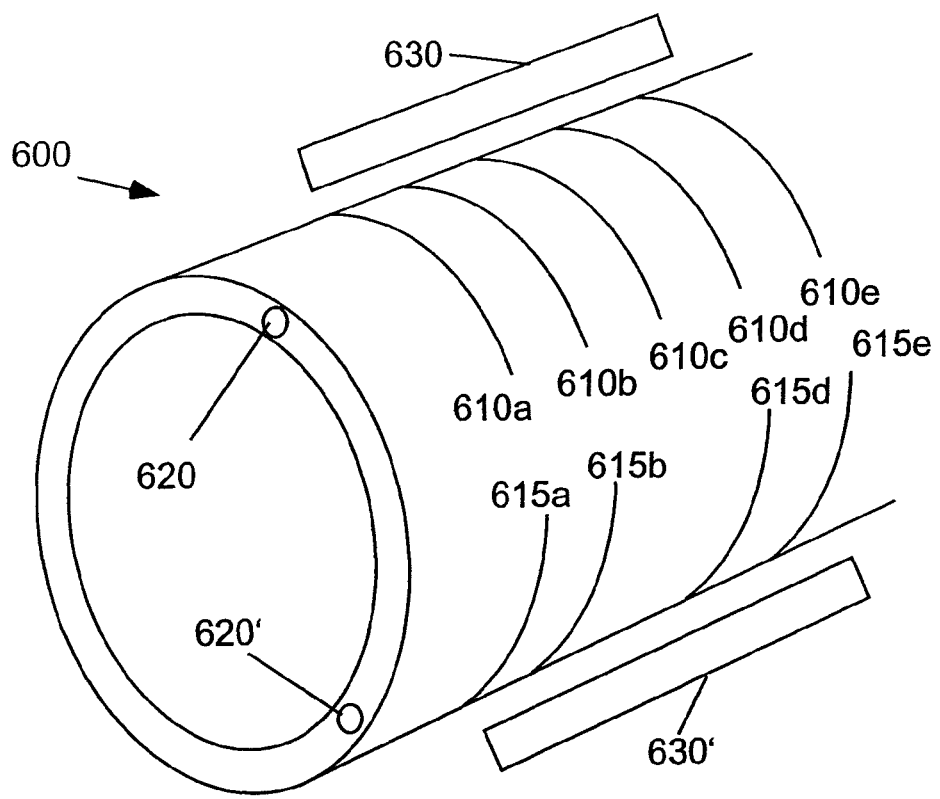
FIG. 4 illustrates a rear perspective view of an embodiment of a syringe encoder including two sets of indicators positioned on different quadrants of the syringe encoder.

As discussed above, the indicators of the present invention can for example extend around the circumference of a syringe or a syringe adapter to a sufficient extent so that the orientation of the syringe, the syringe adapter or the syringe encoder (that is, the degree of rotation about its axis) with respect to the injector, light source and/or sensor bank is irrelevant to the ability of the corresponding sensors to measure how the indicators modify energy propagated through the syringe, the syringe adapter or the syringe encoder. However, orientation can be used to encode more information. FIG. 4, for example, illustrates a syringe encoder 600 including a plurality (two in this embodiment) of sets of indicators to set forth a plurality of binary codes. Indicators 610*a*, 610*b*, 610*c*, 610*d* and 610*e* (the first set) and indicators 615*a*, 615*b*, 615*d* and 615*e* (the second set) are positioned, for example, in different sections or quadrants of generally cylindrical syringe encoder 600. Syringe encoder 600 further includes two light sources 620 and 620' as well as two sensor banks 630 and 630'. Encoder 600 can, for example, be a portion of a syringe wall or a portion of a syringe adapter. Likewise, encoder 600 can be attachable to a syringe or a syringe adapter.

In the embodiment of FIG. 4, at least one indicator in each set of indicators, for example, the last indicator in each set of indicators (that is, indicators 610*e* and 615*e*) can be used to determine if a syringe is properly attached to and/or properly positioned with respect to a powered injector (not shown in FIG. 4). Indicators 610*e* and 615*e* (and/or other indicators) can also be used to check parity and/or to calibrate the sensitivity of sensors 630 and 630', which can, for example, be an array of sensors or a single sensor such as a charge-coupled device (CCD) camera. For example, the indicators of FIG. 4 may be angled notches as discussed in connection with the embodiment of FIG. 2C. The amount of light sensed by sensor banks 630 and 630' as a result of indicators 610*e* and 615*e*, respectively, can provide information for calibrating sensitivity settings for determining whether other indicators are present or absent at various positions on syringe encoder 600.

Dedicating the use of indicators 610*e* and 615*e* as position and/or calibration indicators, the presence or absence of other indicators can be used to set forth binary code(s) of predetermined lengths. In FIG. 4, two binary codes of four bits each are represented by indicators 610*a*, 610*b*, 610*c* and 610*d* of the first set of indicators and by indicators 615*a*, 615*b* and 615*d* of the second set of indicators. The binary code of the first set of indicators is 1111, while the binary code of the second set of indicators is 1101 (an indicators at the third or "c" position is absent in the second set of indicators). The two binary codes correspond to a particular syringe configuration as can be provided, for example, in a look-up table stored in computer memory. With the use of a sensor or sensors having a relatively wide detection range (for example, a CCD camera) the absolute position of a set of indicators representing a binary code is not as important as the case in which sensors have a relatively narrow range of detection are used, requiring general alignment of an indicator/sensor pairing.

Figure 5A:
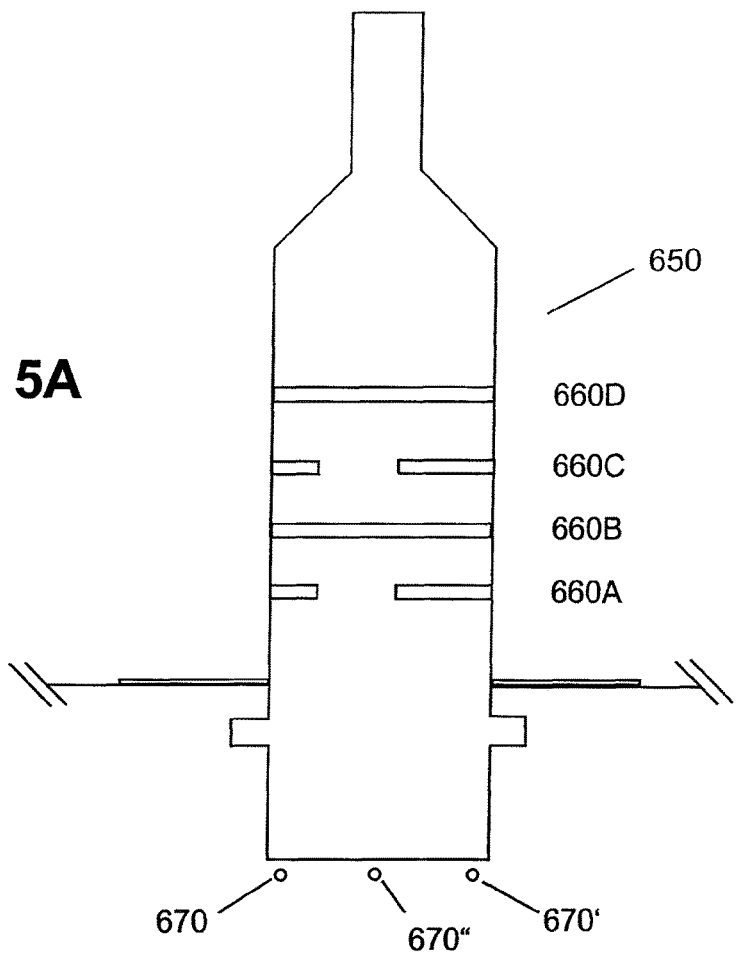
FIG. 5A illustrates a side view of an embodiment of a syringe including multiple sets of indicators.
Figure 5B:
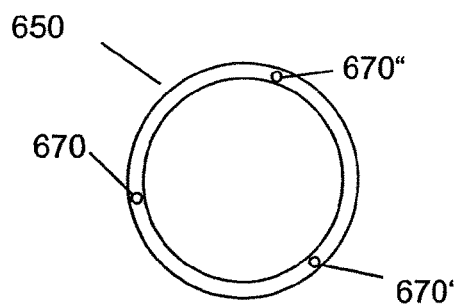
FIG. 5B illustrates a bottom view of the syringe of FIG. 5A.

FIGS. 5A and 5B illustrate another embodiment of the present invention (similar to that of FIG. 4) in which several bands of indicators 660A, 660B, 660C and 660D extend at least partially around the circumference of a syringe 650 at predetermined positions along the length of syringe 650. As illustrated in FIG. 5B, three energy sources 670, 670' and 670" are positioned at different positions around the circumference of syringe 650 adjacent the rearward end of syringe 650. Four detectors (not shown in FIGS. 5A and 5B) can be placed in general alignment with sources 670, 670' and 670" at each band level of indicators (four bands×three sources=twelve detectors in total). Dedicating, for example, the D-band of indicators to position and/or calibration determinations as described above, one is left with three binary codes of three bits each or 216 possible different encoded configurations.

Figure 6:
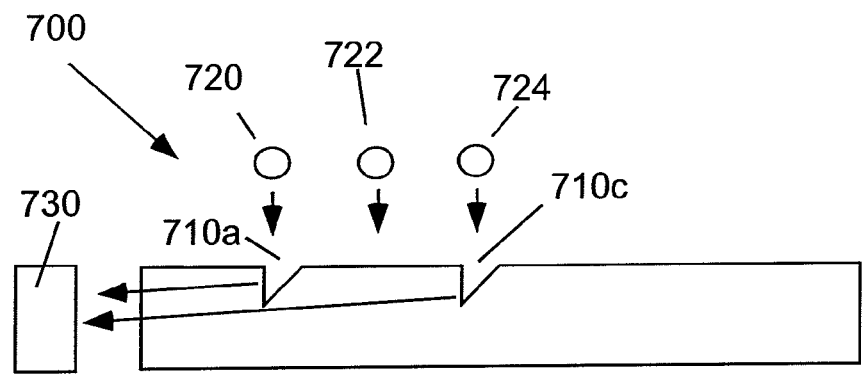
FIG. 6 illustrates a side cross-sectional view of a syringe encoding system in which energy signals are pulsed.
Figure 6:
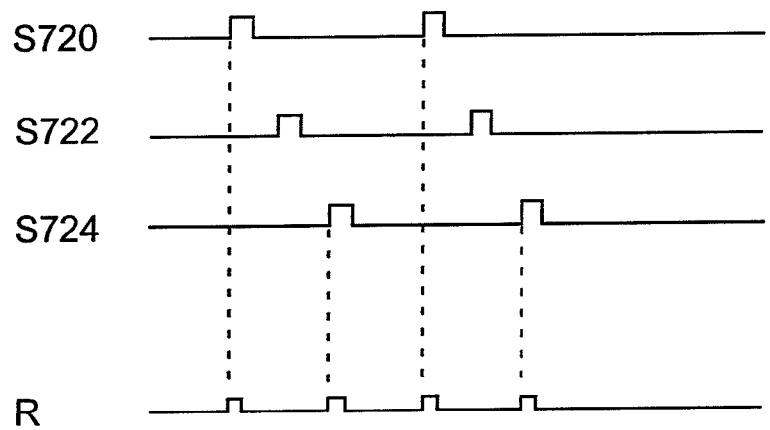

In FIG. 6, a syringe encoder 700 includes indicators 710*a* and 710*c* that are angled surfaces formed in the surface of syringe encoder 700. Three energy sources 720, 722, 724 are pulsed sequentially as shown in the timing diagram of FIG. 6 as waveforms S720, S722, S724. S720 and S724 are positioned over indicators or grooves 710*a* and 710*c*, respectively, in the syringe barrel, which transmit light to a receiver 730. In the embodiment of FIG. 6, there is no indicator on the syringe corresponding to the fixed position of energy source 720. No energy is, therefore, transmitted to receiver 730 when S722 is pulsed on. Consequently, the reception portion R of the timing diagram shows pulses received from S720 and S724 but not from S722. The presence or absence of indicators at each source can represent a digital code as described above.

Figure 7:
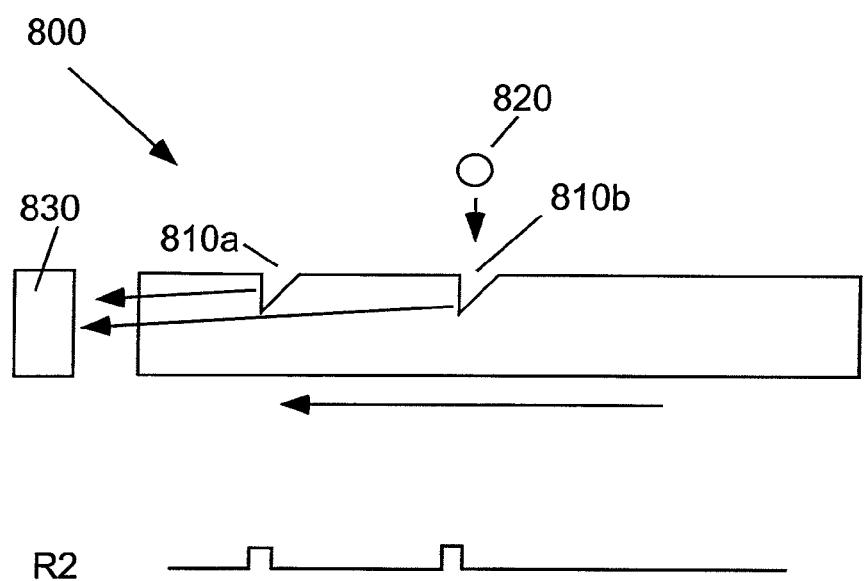
FIG. 7 illustrates a side cross-sectional view of a syringe encoding system in which syringe configuration is determined in a dynamic fashion.

In the above discussion, syringe configuration information is read in a static fashion. Syringe configuration information can also be read in a dynamic fashion using the syringe encoding systems of the present invention. As syringe encoder 800 is moved to the left in the orientation of FIG. 7 (for example, as a syringe is attached to a powered injector), indicators 810*a* and 810*b* redirect at least a portion of light energy from light source 820 through syringe encoder 800 to a receiver 830 as illustrated with arrows in FIG. 7. A received signal R2 provides information on syringe configuration.

Figure 8:
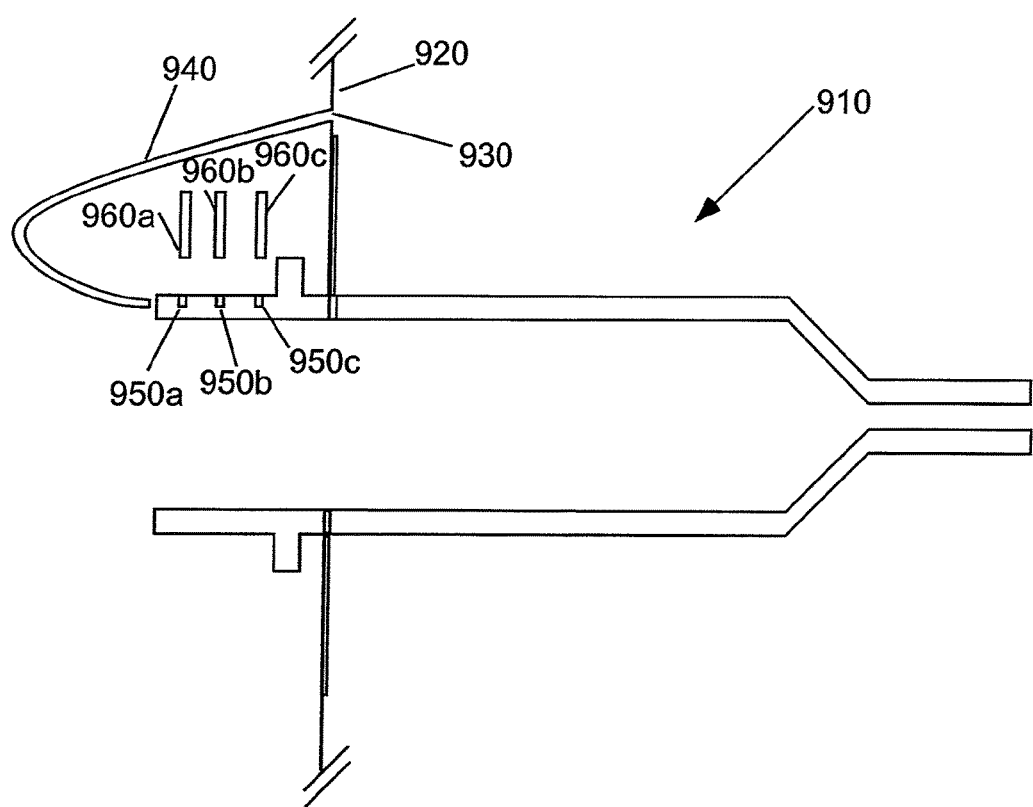
FIG. 8 illustrates side cross-sectional view of a syringe using ambient light as a light source for syringe encoding.

In the case that light energy is used in the present invention, the light source can be a powered light source such as an LED or other powered light source as known in the art. However, ambient light can also be used. In FIG. 8, for example, a syringe 910 is attached to a powered injector 920. Powered injector 920 includes an opening 930 through which ambient light can pass. Opening 930 is in communicative connection with, for example, a fiber optic cable 940. Fiber optic cable 940 terminates adjacent a rearward end of syringe 910 and provides light energy to one or more indicators 950*a*, 950*b* and 950*c*. As discussed above, detectors 960*a*, 960*b* and 960*c* are adapted to sense modification of the light energy by indicators 950*a*, 950*b* and 950*c*, respectively.

Model Studies

In the case that the indicators of the present invention use refraction and/or reflection to direct light energy to corresponding detectors, the design (for example, position, depth and angle) of the indicators can have substantial effect on the light detected by the detectors. To study these and other effects in several designs of the present invention, a ray-tracing model was constructed using Mathcad software, available from MathSoft of Cambridge, Mass. In this software, the intensity of reflected or refracted rays is varied with the angle of incidence according to Fresnel's laws.

In the models, the syringe or encoder was assumed to be rotationally symmetric and its cross-section was described by a closed polygon. The syringe material was assumed to be optically uniform and isotropic, with a refractive index of 1.68. A nominal value of 3 dB per inch was used for optical attenuation within the syringe material.

A point light source was used with a Gaussian beam profile. The source was placed 0.2 inches from the rear/bottom edge of the syringe and a half-power beam half-angle of 5° was used. To test each design, about 500 rays from the source were traced.

Each ray was traced to its first point of incidence, and the attenuation over that distance was taken into account. The transmitted and reflected rays were calculated according to Fresnel's laws. The transmitted and reflected rays were then traced independently, each yielding new transmitted and reflected rays at their next incidence. This iterative process quickly generated many rays from the first ray. A ray was terminated when it either finally exited the syringe or its intensity dropped below a threshold value. The rays that exited the syringe were collected on an imaging surface, a cylinder placed around the syringe at a radius corresponding a likely position of sensors as described above. The point and angle of incidence were recorded, as well as the intensity of the ray.

In addition to the assumptions or conditions stated above, the model ignored the following effects or conditions: the presence of a piston head at the inside wall of the syringe; the presence of any contrast medium in the syringe cavity; and surface roughness of the syringe.

Two forms of graphical output were generated. First, all of the rays generated by a single ray were superimposed on a three-dimensional plot of the syringe. This output facilitated debugging of the code and was useful in tracking down undesirable features of particular designs. Second, a surface plot of light intensity on the image plane was generated. As an option, one can choose only those rays that hit the image plane within a certain angle of incidence to contribute to the plotted intensity. This output illustrates the overall performance of a design.

Figure 9:
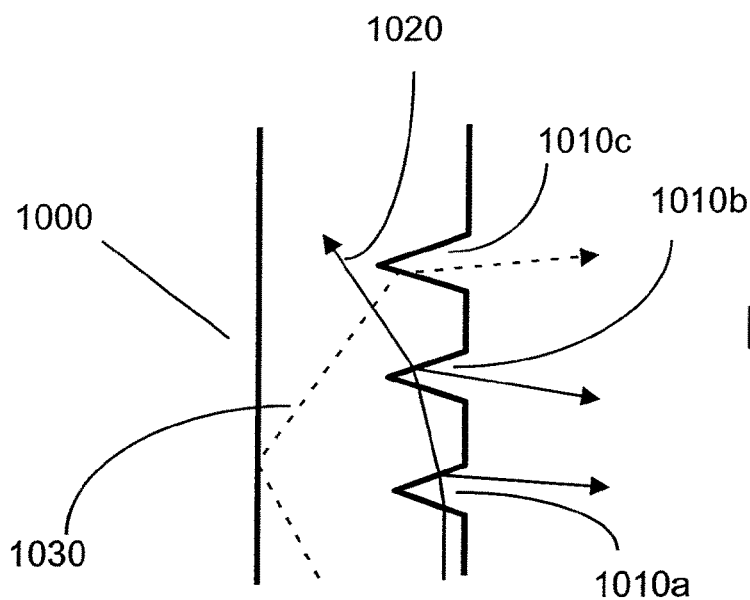
FIG. 9 illustrates a model study of a syringe encoder with angled notches.

FIG. 9 illustrates, for example, a portion of a syringe or an encoder 1000 in which the indicators are V-shaped notches 1010a, 1010b and 1010c. In FIG. 9, a light source (not shown) is positioned at the bottom of syringe 1000. In this embodiment, it is difficult to make notches 1010a, 1010b and 1010c perform independently of each other (that is, light from one notch depends on the presence or absence of the notches preceding it or below it in the orientation of FIG. 9). In that regard, the section of the syringe wall between two notches resembles generally a prism. When light traveling generally parallel to the syringe wall passes through this prism it is bent off-axis, away from the notches above it. For example, a refracted ray 1020 is bent away from notch 1010 c in FIG. 9, when passing through the syringe wall between notches 1010b and 1010c. The illumination of notch 1010c above the prism of the syringe wall in this case must rely on rays internally reflecting off the inside surface of syringe 1000. In that regard, another ray 1030 is shown to internally reflect within the syringe wall to contact notch 1010c. In the embodiment of FIG. 9, it is difficult to ensure that internally reflected rays that exit a notch by refraction and rays traveling through the notches that exit by reflection leave a notch at similar angles. This result can easily lead to cross-talk between detector-indicator pairs, wherein the light from one notch reaches more than one detector as discussed above. As also discussed above, the use of columnators can reduce the effects of this problem.

However, the interdependence between the V-shaped notches makes it complicated to choose a notch shape that works well for all the notch codes. Moreover, the use of refraction also makes the design sensitive to the refractive index of the material.

Figure 10:
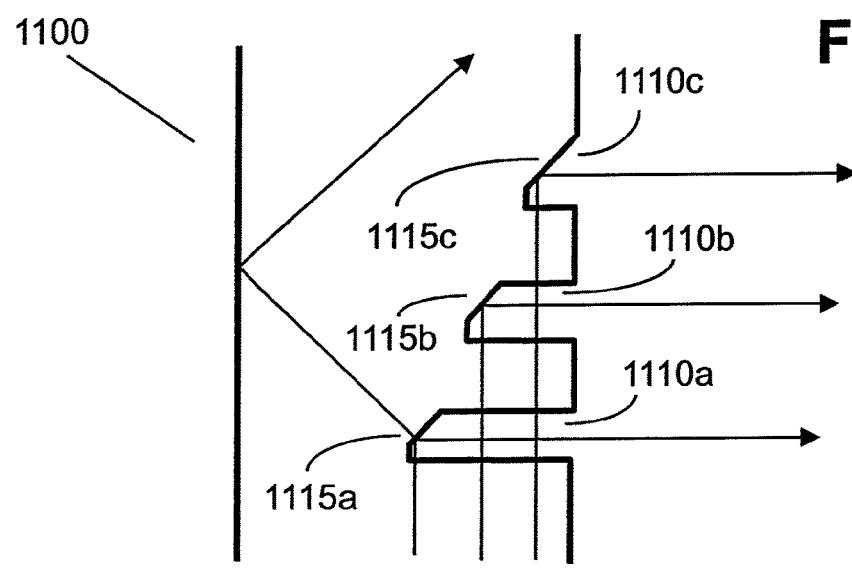
FIG. 10 illustrates a model study of a syringe encoder with reflective surfaces.

These problems can be substantially eliminated by using transmission of energy at near normal incidence to an indicator surface and reflection as illustrated in FIG. 10. Syringe 1100 includes three indicator notches 1110a, 1110b and 1110c. Indicator notches 1110a and 1110b include two generally parallel walls and a reflecting surface or wall 1115a and 1115b, respectively, oriented at generally 45° to light rays incident thereupon, resulting in reflection of the incident light rays at an angle approximately 90° to the direction of the incident light rays. Shallower indicator notch 1015c also includes a reflecting surface 1115c that is also oriented at generally 45° to light ray incident thereupon. Reflector surfaces 1115a, 1115b and 1115c reflect light to appropriately positioned detectors (not shown in FIG. 10). In practice, the generally parallel walls of indicator notches 1110a and 1110b preferably have a draft angle to allow a mould tool to be released in the case of an injection molded syringe. A small angle of approximately 2° is likely sufficient and will not significantly affect the optical properties of indicator notches 1110a and 1110b.

Because reflector surfaces 1115a, 1115b and 1115c are offset or positioned at different depths within the syringe wall and reflection rather than refraction is used to transmit light from indicator notches 1110a, 1110b and 1110c to corresponding detectors, it is possible for indicator notches 1110a, 1110b and 1110c to affect the light energy generally independently of each other. Moreover, the design of FIG. 10 is substantially insensitive to the refractive index of the syringe material.

The only remaining interdependent effect between indicator notches 1110a, 1110b and 1110c is the reduction of the intensity of light energy as it is transmitted through the notch walls. Taking multiple reflections into account, the intensity of the transmitted light is reduced by about 13% (for a refractive index of 1.68) after passing through each notch. The reduction amounts to 50% after passing through four indicator notches. One can compensate for such a reduction in intensity by increasing the size of the 45° reflector surfaces of indicator notches as one proceeds further down the axis or length of syringe 1100. Accurately, balancing the brightness of each indicator notch may thus involve changing the size of each reflector surface according to the particular binary code involved, (that is, according to the presence or absence of the preceding indicator notches).

Figure 11:
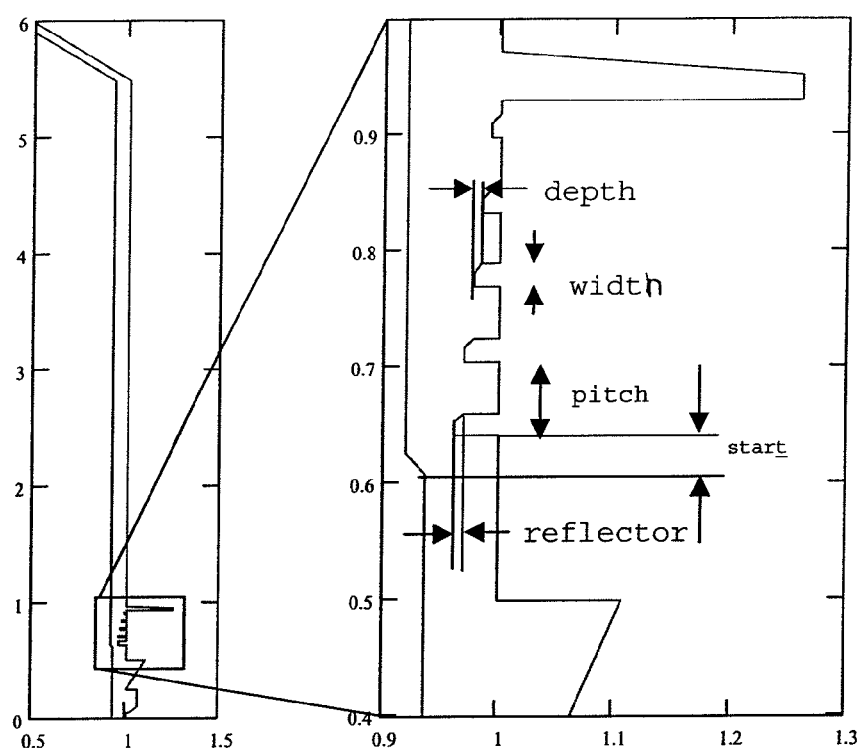
FIG. 11 illustrates dimensions of one embodiment of a model syringe design.

A representative model of the embodiment of FIG. 10 is illustrated in FIG. 11. Several preferred constraints were incorporated in the model of FIG. 11. For example, the maximum notch depth was set to half of the syringe wall thickness to maintain structural integrity. If the difference in depth between two neighboring indicator notches is less than the radial width of the reflector surface, then the reflector surface of the first notch will partially shadow the reflector surface of the second notch, reducing the amount of light reflected from the second notch. This effect is partially compensated by rays reaching the reflector surfaces via internal reflection off the outside surface of the syringe wall as shown in FIG. 10. However, a lower limit is preferably set on the increment in depth from one notch to the next. A minimum notch width of approximately 0.5 mm was set according to the thinnest section that can be used in a certain molding tool. The minimum notch width limits the size of the reflector surface, and hence the amount of light reflected from each reflector surface. Minimum spacing between notches is preferably set to eliminate cross-talk. In one model, the maximum spacing possible was chosen. It is also desirable to avoid secondary reflections. In other words, it is desirable that the refracted ray from each reflector surface should not subsequently hit the reflector surfaces further down the syringe, as shown in FIG. 10. This is a more complicated geometric constraint that also involves the refractive index of the syringe.

FIG. 11 illustrates the dimensions of the model design, in which the parameters are the same for each notch, apart from depth, which had a fixed increment from one notch to the next. The selected dimensions were: (1) pitch: 0.064 in., (2) width 0.020 in., (3) start 0.032 in., (4) reflector surface size: 0.008 in.; and (5) depth increment: 0.008 in. The depth of the first indicator notch was set as the reflector size plus 4× (depth increment), which is approximately 0.040 in (or approximately 1 mm), or approximately half of the syringe wall thickness. The syringe wall can be thickened in the region of the indicator notches to preserve the mechanical strength of the syringe.

Figure 12:
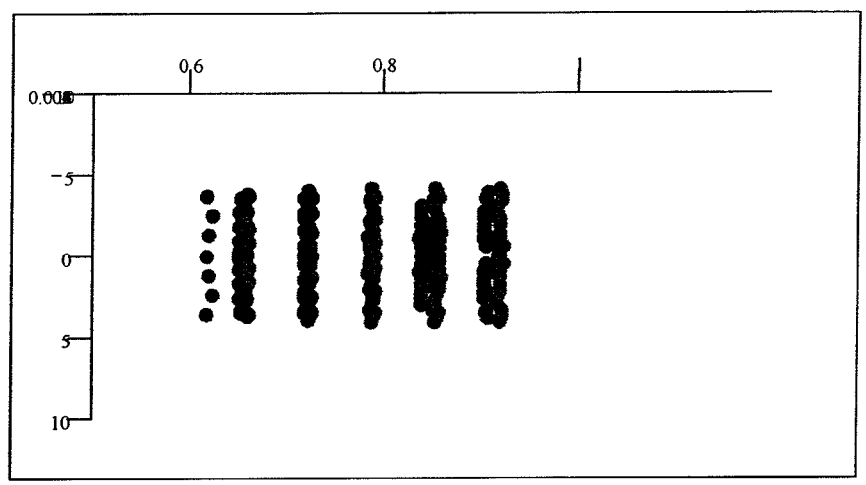
FIG. 12 illustrates the result of tracing light rays through the model syringe of FIG. 11.

In the model, a cylindrical image plane was placed at a radius of approximately 1.15 inches. FIG. 12 illustrates the result of tracing 500 rays through the syringe and shows the position of the endpoints of the rays on the cylindrical image plane, with the Z-coordinate plotted in inches on the horizontal axis and the angle around the cylinder plotted in degrees on the vertical axis.

Five main image areas can be identified, one for each indicator notch. The leftmost image area is much weaker than the image areas corresponding to the indicator notches and is a result of light scattering off a guide or positioning element at the bottom of the syringe. The light scattering off of the positioning element is incident on the image cylinder at an angle of 40°, whereas light rays from the indicator notches are incident at angles of 10° or less. Differences in incident angle and/or differences signal strength (as, for example, compared to threshold values) can be used to eliminate artifacts. Light from sources other than indicators (for example, the scattered light giving rise to leftmost area or artifact in FIG. 12) can also be prevented by placing an optical stop 1120 at the bottom of the syringe as illustrated in FIG. 13 or it can be blocked, for example, by using collimated detectors.

Figure 13:
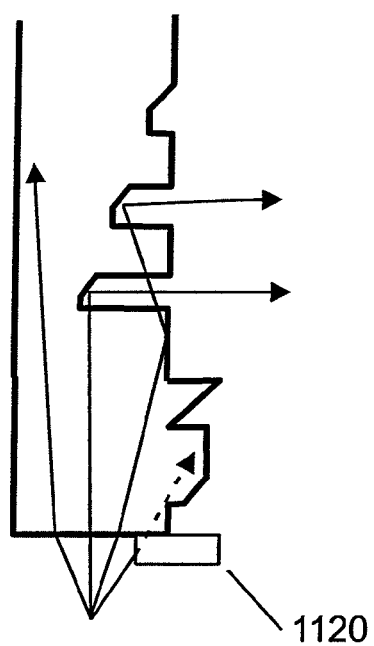
FIG. 13 illustrates examples of light rays reflecting off indicators that originate from a combination of direct incidence and incidence via internal reflection.

In FIG. 12, the image areas from the last two indicator notches are noticeably broadened as the rays that reflect off those indicator notches originate from a combination of direct incidence and incidence via internal reflection off the outer surface of the syringe as represented in FIG. 13.

Figure 14:
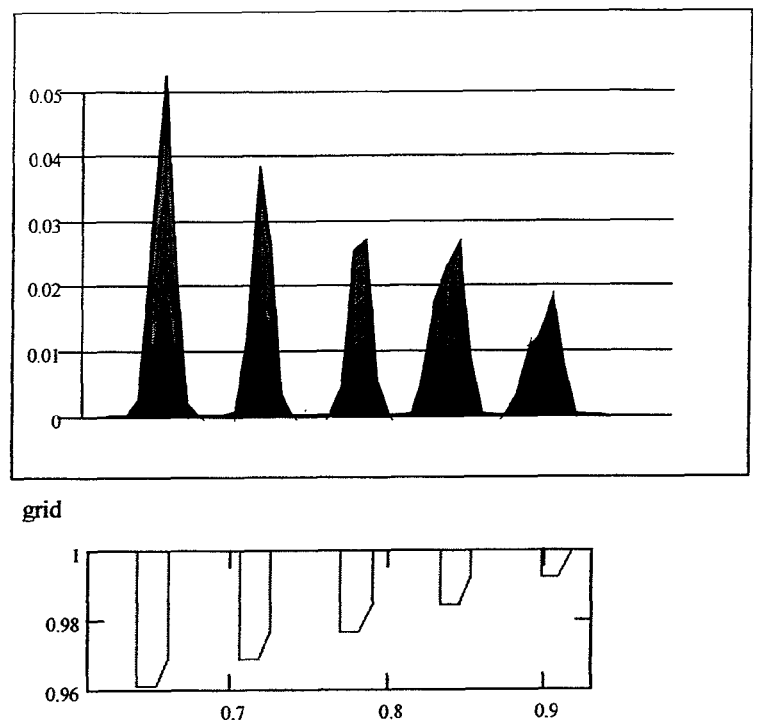
FIG. 14 illustrates the total brightness of each spot on an imaging cylinder shown above its corresponding indicator notch for the model design of FIG. 11.

FIG. 14 shows the total brightness of each spot on the imaging cylinder, shown above its corresponding indicator notch. There was a 3:1 ratio between the brightness of the first indicator notch image and that of the last. It is possible to adjust this by progressively increasing the reflector sizes from first to last.

Figure 15:
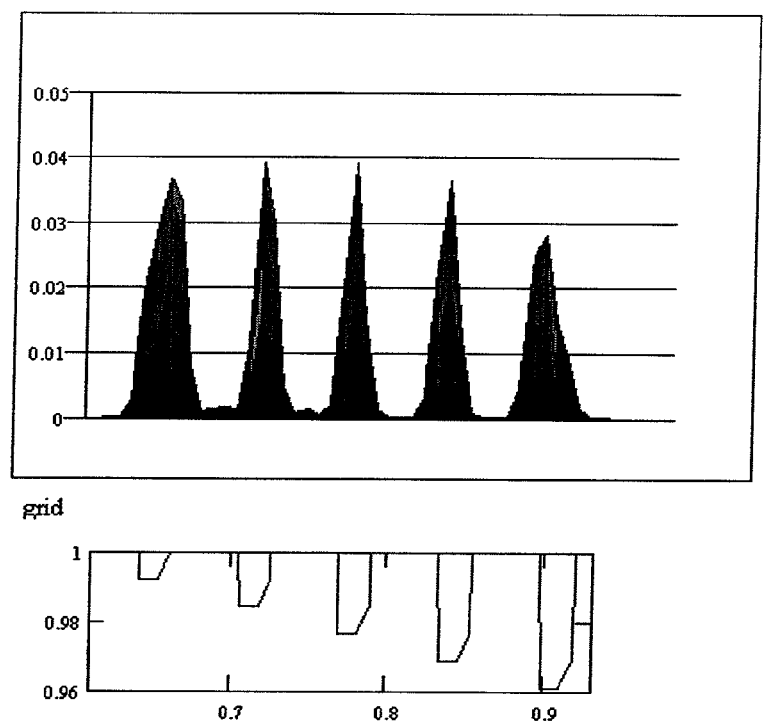
FIG. 15 illustrates the total brightness of each spot on an imaging cylinder shown above its corresponding indicator notch for a model design in which the order of indicator notches is reversed from that of FIG. 14.

Alternatively, by reversing the order of the indicator notches such that the shallowest indicator notch is placed closest to the energy source and the deepest indicator notch is places farthest from the energy source, brightness/intensity reductions can be substantially eliminated. In that regard, FIG. 15 shows the total brightness of each spot on the imaging cylinder, shown above its corresponding indicator notch in such an embodiment. As illustrated, there is very little reduction in brightness between the first indicator notch and the last indicator notch in this embodiment.

Preferably, light transmitted to a sensor (as measured, for example, in brightness or signal strength) is sufficient such that the interaction of light with an indicator is readily detectable using commercially available, inexpensive sensors and light sources. An example of a suitable sensor for use in the present invention is the SFH229FA (part number) photodiode available from OSRAM, a multinational corporation headquartered in Munich, Germany. An example of a suitable light source for use in the present invention is the HSDL-4230 (part number) LED available from Hewlett-Packard, a multinational corporation headquartered in Palo Alto, Calif.

Figure 16A:
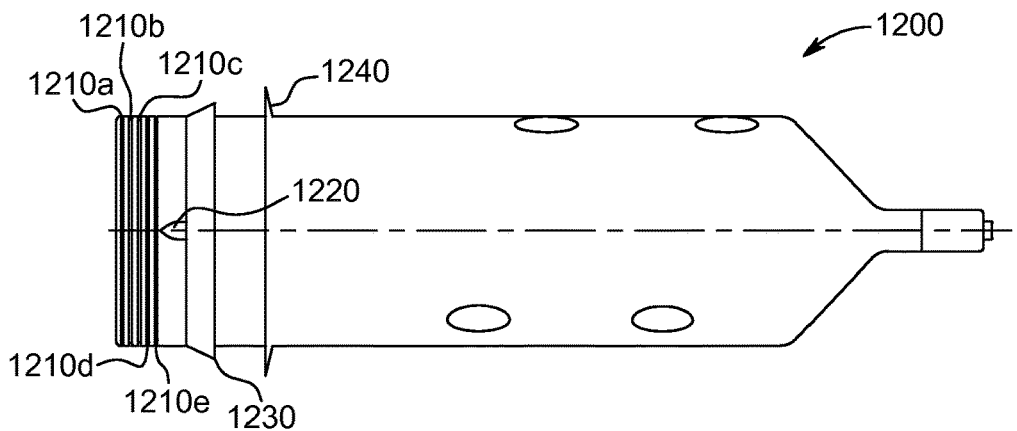
FIG. 16A illustrates a side view of an embodiment of a syringe of the present invention in which the depth of indicator notches increases with increasing distance from a light source.
Figure 16B:
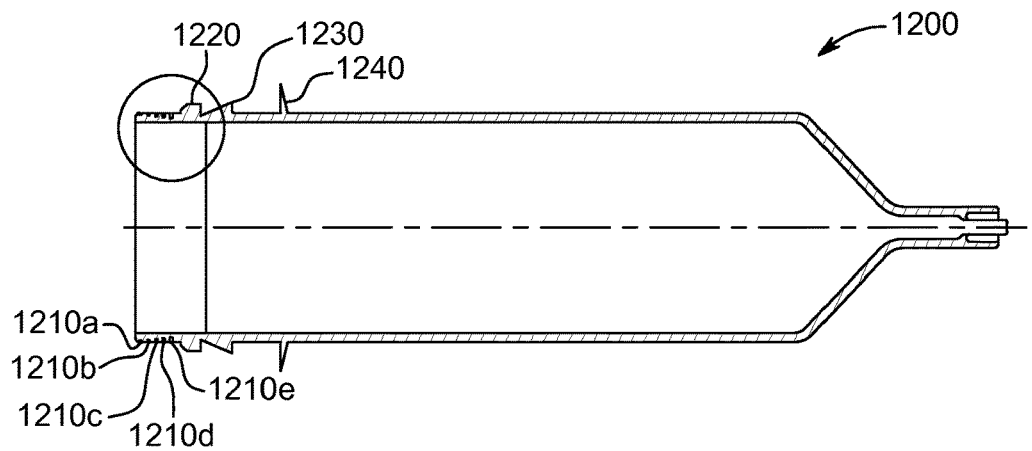
FIG. 16B illustrates a side, cross-sectional view of the syringe of FIG. 16A.
Figure 16C:
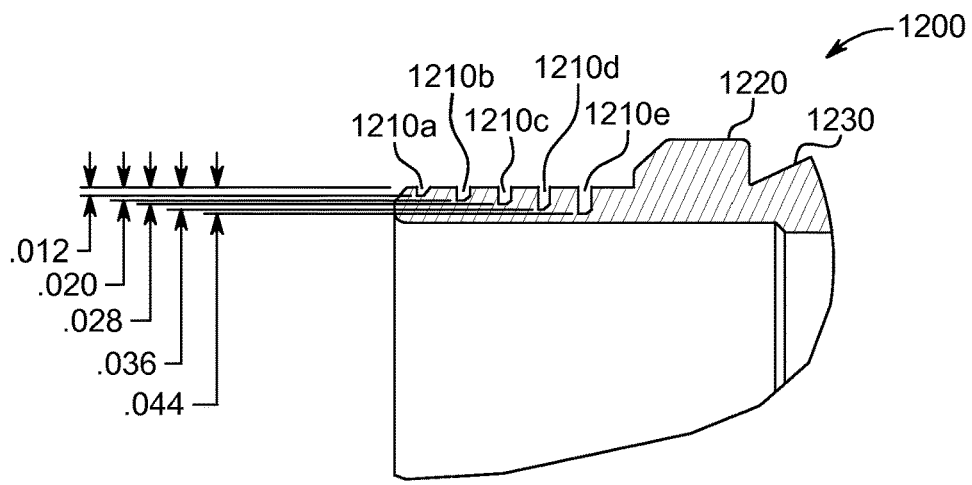
FIG. 16C illustrates an expanded view of the encircled area of FIG. 16B.

FIGS. 16A through 16C illustrate an embodiment of a syringe 1200 in which indicator notches 1210a through 1210e increase in depth with increasing distance from a light source (not shown in FIGS. 16A through 16C) as described in connection with FIG. 15. FIG. 16C illustrates an expanded view of indicator notches 1210a through 1210e (that is, the encircled portion of FIG. 16B) and provides depth dimensions thereof (in inches) for one embodiment of syringe 1200. In that embodiment, the depth of indicator notches 1210a through 1210e are, 0.012 in, 0.020 in. 0.028 in, 0.036 in and 0.044 in, respectively. Indicator notches 1210a through 1210e are preferably placed at a rearward position on syringe 1200 to position indicator notches 1210a through 1210e as close as possible to the light source as well as to reduce or prevent artifacts arising from other syringe components. For example, positioning elements 1220, engagement flange 1230 and drip flange 1240 can each cause artifacts in an image plane as illustrated, for example, by the leftmost image area of FIG. 12. Placing indicator notches 1210a through 1210e between the energy/light source and such syringe components greatly reduces the likelihood of undesirable artifacts.

Figure 16D:
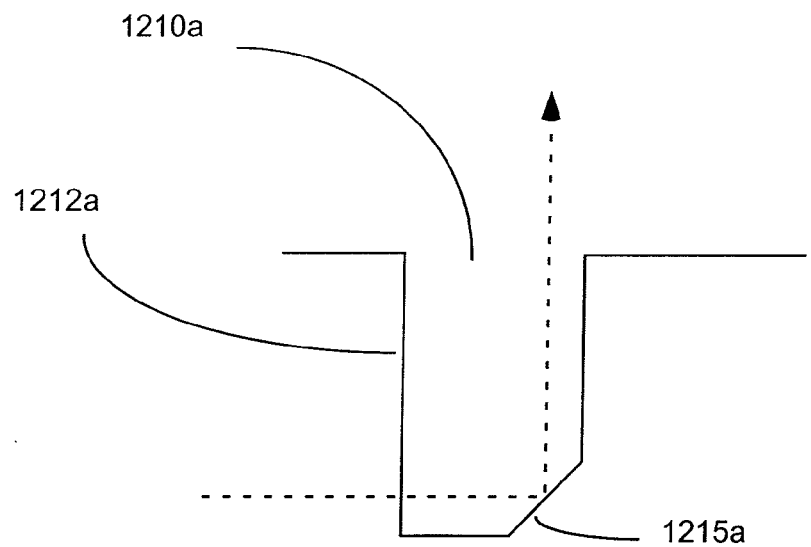
FIG. 16D illustrates an expanded view of one of the indicator notches of FIGS. 16A through 16C.
Figure 16E:
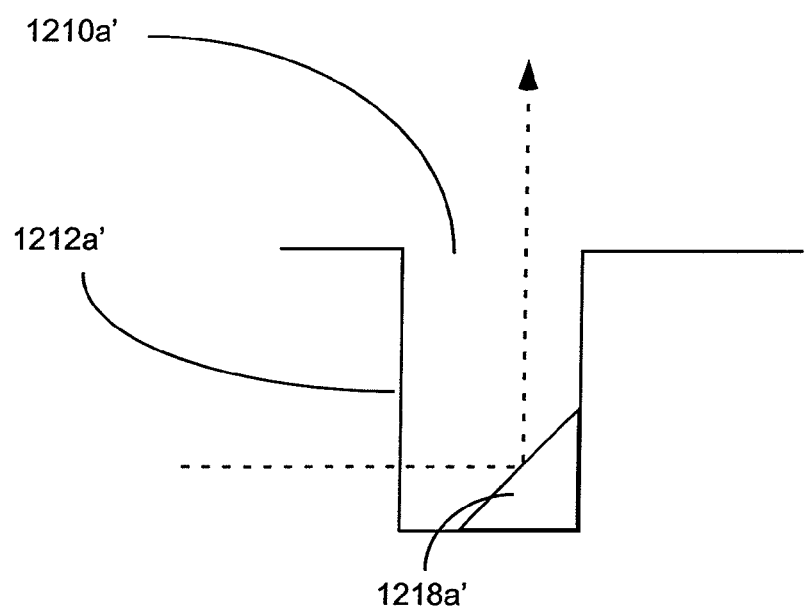
FIG. 16E illustrates an embodiment of an indicator notch including an attached reflective surface.

FIG. 16D illustrates an expanded view of indicator notch 1210a of FIGS. 16A through 16C. As illustrated in FIG. 16D, a light ray first passes through a generally perpendicular wall 1212a of indicator notch 1210a and then passes through the air to impinge upon surface 1215a, which reflects the light ray upward to a sensor (not shown in FIG. 16D). Surface 1215a in FIG. 16D is a portion of the syringe wall angled at an approximately 45° angle to light rays propagating lengthwise through the wall of syringe 1200. FIG. 16E illustrates another embodiment of an indicator notch 1210a'. In the embodiment of FIG. 16E, a light ray first passes through a generally perpendicular wall 1212a' of indicator notch 1210a' and then passes through the air to impinge upon surface 1215a', which reflects the light ray upward to a sensor (not shown in FIG. 16E). In the embodiment of FIG. 16E, reflective surface 1215a' is formed of a different material (preferably, a highly reflective material) than the material of syringe 1200.

Figure 17:
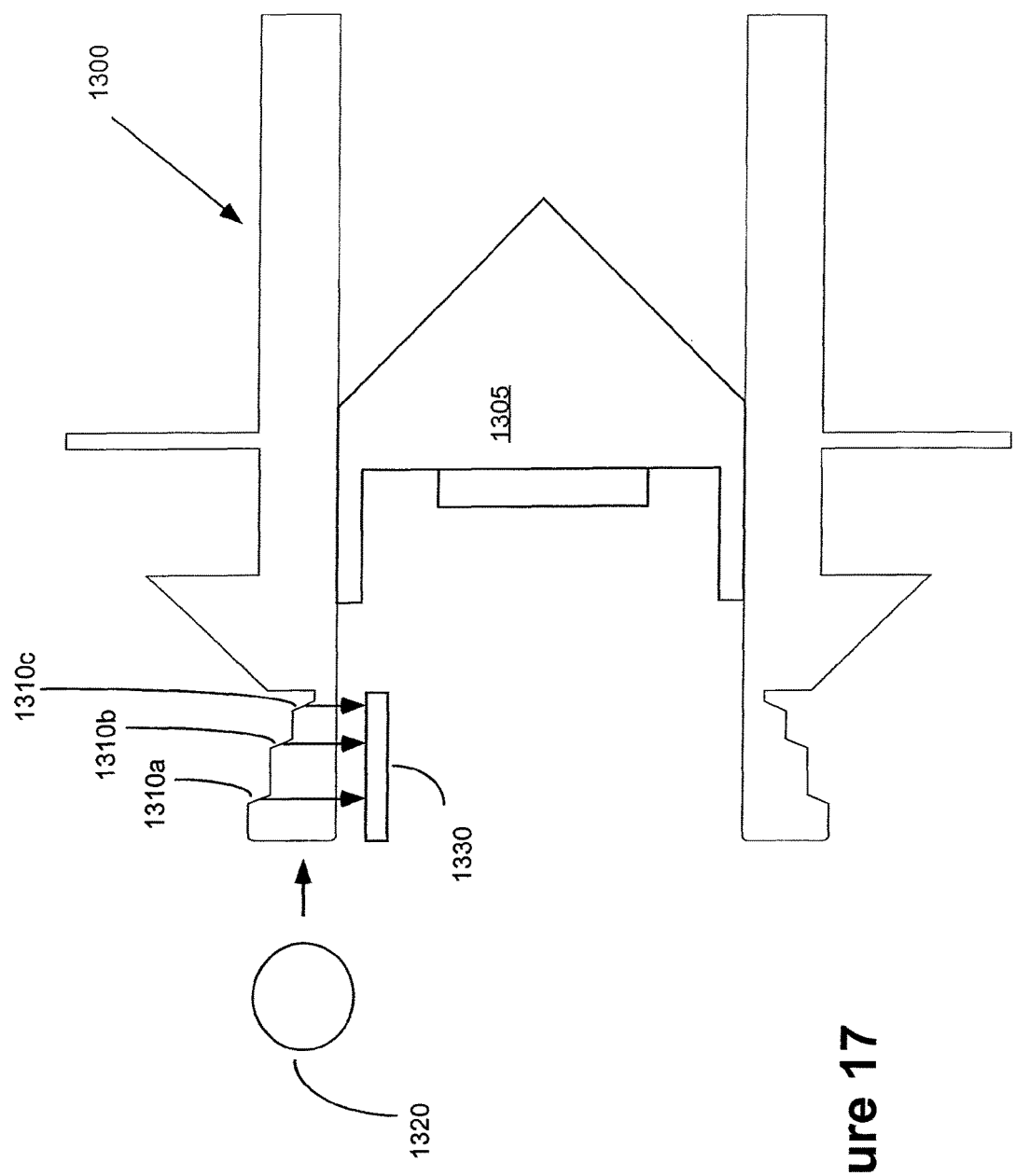
FIG. 17 illustrates a side, cross-sectional view of an embodiment of a syringe in which indicators redirect energy to one or more sensors positioned within the interior of the syringe.

FIG. 17 illustrates an embodiment of a rear portion of a syringe 1300 including indicators 1310a-1310c formed as angled steps in the exterior wall of syringe 1300. In one embodiment, indicators 1310a-1310c are angled at approximately 45° with respect to light rays propagated through the wall of syringe 1300 from light source 1320. In this embodiment, light rays from light source 1320 are reflected at an angle of approximately 90° with respect to the orientation through which the light is propagated through the wall of syringe 1300 toward a sensor or sensors 1330 positioned on the interior side of the syringe wall. Reflection of light at generally right angles can facilitate positioning of a corresponding sensor or sensors for detection of reflected light. In this embodiment, indicators 1310a-1310c affect the light energy generally independently of each other. Preferably, sensor or sensors 1330 are positioned within the interior of the barrel of syringe 1300 to minimize or prevent interference with the movement of a plunger 1305 within the syringe barrel.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A syringe, comprising:
   a syringe body comprising a sidewall defining a longitudinal axis, wherein at least a portion of the sidewall is configured to propagate electromagnetic energy emitted from an electromagnetic source incident on the sidewall by internal reflection in a direction substantially parallel to the longitudinal axis; and
   at least one indicator recessed radially into an outer surface of the sidewall,
   wherein the at least one indicator is adapted to reflect at least a portion of the electromagnetic energy radially from the sidewall such that the reflected energy is detectable by a sensor to provide information about one or more parameters.

2. The syringe of claim 1, wherein the at least one indicator has a reflective surface adapted to reflect the electromagnetic energy.

3. The syringe of claim 2, wherein the reflective surface is positioned to reflect the electromagnetic energy at an angle of approximately 90°.

4. The syringe of claim 1, further comprising at least two indicators located at different longitudinal positions along the sidewall.

5. The syringe of claim 4, wherein the longitudinal position of the at least two indicators provides information about the syringe.

6. The syringe of claim 1, wherein the at least one indicator is formed integrally with the syringe.

7. The syringe of claim 1, wherein the at least one indicator provides information about the syringe.

8. An injector system, comprising:
   a powered injector; and
   a syringe adapted to interface with the powered injector, the syringe comprising:
      a syringe body comprising a sidewall defining a longitudinal axis, wherein at least a portion of the sidewall is configured to propagate electromagnetic energy emitted from an electromagnetic source incident on the sidewall by internal reflection in a direction substantially parallel to the longitudinal axis; and
      at least one indicator recessed radially into an outer surface of the sidewall,
      wherein the at least one indicator is adapted to reflect at least a portion of the electromagnetic energy radially from the sidewall such that the reflected energy is detectable by a sensor to provide information about one or more parameters.

9. The injector system of claim 8, wherein the at least one indicator has a reflective surface adapted to reflect the electromagnetic energy.

10. The injector system of claim 8, further comprising at least two indicators located at different longitudinal positions along the sidewall.

11. The injector system of claim 8, wherein the at least one indicator is formed integrally with the syringe.

* * * * *

UNITED STATES PATENT AND TRADEMARK OFFICE
CERTIFICATE OF CORRECTION

PATENT NO. : 10,060,758 B2
APPLICATION NO. : 14/329050
DATED : August 28, 2018
INVENTOR(S) : Cowan et al.

Page 1 of 1

It is certified that error appears in the above-identified patent and that said Letters Patent is hereby corrected as shown below:

In the Drawings
In Fig. 16E, Sheet 21 of 22, delete Tag "1218a'" and insert Tag -- 1215a' --, therefor.

Signed and Sealed this
Twentieth Day of November, 2018

Andrei Iancu
*Director of the United States Patent and Trademark Office*